(12) United States Patent
Murdock et al.

(10) Patent No.: US 7,068,362 B2
(45) Date of Patent: Jun. 27, 2006

(54) EXPENDABLE BEAM TRANSMISSOMETER

(75) Inventors: Thomas M. Murdock, Eldersburg, MD (US); Kirk S. Decker, Catonsville, MD (US); James T. Velky, Baltimore, MD (US); Karen D. Rennich, Elkridge, MD (US)

(73) Assignee: The Johns Hopkins University, Baltimore, MD (US)

( * ) Notice: Subject to any disclaimer, the term of this patent is extended or adjusted under 35 U.S.C. 154(b) by 232 days.

(21) Appl. No.: 10/348,890

(22) Filed: Jan. 22, 2003

(65) Prior Publication Data
US 2003/0174317 A1    Sep. 18, 2003

Related U.S. Application Data

(60) Provisional application No. 60/351,351, filed on Jan. 25, 2002.

(51) Int. Cl.
*G01J 1/44* (2006.01)
*G01N 21/00* (2006.01)

(52) U.S. Cl. .................. 356/226; 356/432; 356/218

(58) Field of Classification Search ................ 356/213, 356/218, 226, 432–440, 152.3; 250/573–575
See application file for complete search history.

(56) References Cited

U.S. PATENT DOCUMENTS

| | | | | |
|---|---|---|---|---|
| 3,850,529 A | 11/1974 | Brugger | ...................... | 356/207 |
| 3,885,162 A | 5/1975 | Geertz | ......................... | 250/573 |
| 3,917,957 A * | 11/1975 | Ansevin et al. | ............. | 250/573 |
| 3,976,369 A | 8/1976 | McCardell | ................... | 350/319 |
| 3,976,891 A | 8/1976 | Parkinson | ................... | 250/575 |
| 3,994,601 A | 11/1976 | Brugger | ..................... | 356/201 |
| 4,017,193 A | 4/1977 | Loiterman | ................... | 356/206 |
| 4,637,719 A | 1/1987 | Herman | ........................ | 356/72 |
| 4,713,964 A | 12/1987 | Ioannides | ..................... | 73/116 |
| 4,891,519 A | 1/1990 | Nohira | ........................ | 250/349 |
| 4,937,461 A * | 6/1990 | Traina | ........................ | 250/575 |
| 5,028,790 A | 7/1991 | McGowan | ................... | 250/573 |
| 5,077,480 A * | 12/1991 | Traina | ........................ | 250/575 |
| 5,181,082 A | 1/1993 | Jeannotte | .................... | 356/436 |
| 5,202,560 A | 4/1993 | Koch | .......................... | 250/238 |
| 5,307,146 A | 4/1994 | Porter | ........................ | 356/320 |
| 5,345,243 A * | 9/1994 | Levis | ........................ | 342/173 |
| 5,418,615 A | 5/1995 | Doyle | ........................ | 356/436 |
| 5,610,713 A | 3/1997 | Heyn | ......................... | 356/342 |
| 5,618,495 A | 4/1997 | Mount | .................... | 422/82.05 |
| 5,696,592 A | 12/1997 | Kuan | ......................... | 356/436 |
| 5,770,389 A | 6/1998 | Ching | ......................... | 435/92 |
| 5,781,305 A | 7/1998 | Downes | ..................... | 356/435 |
| 5,831,730 A * | 11/1998 | Traina et al. | ............... | 356/336 |
| 6,240,305 B1 | 5/2001 | Tsuchiya | .................... | 600/310 |
| 6,781,695 B1 * | 8/2004 | Hovan et al. | ............... | 356/437 |

* cited by examiner

*Primary Examiner*—Layla G. Lauchman
(74) *Attorney, Agent, or Firm*—Benjamin Y. Roca

(57) ABSTRACT

The present invention provides apparatus for a beam transmissometer. In an embodiment, the beam transmissometer includes a LED signal source, collimating apparatus, a retroreflector that directs the projected beam, imaging apparatus that directs the beam onto a detector that converts the projected beam into an electrical signal, and signal processing circuitry that enhances the reception of the optical beam. The LED signal source is modulated in a pulsed fashion so that the effects of beam reflection are ameliorated. Signal processing circuitry amplifies, filters, and synchronizes to the electrical signal. A calculating unit uses the processed signal to determine a beam attenuation coefficient, which is indicative of the visibility of a medium in which the transmissometer is immersed. A method is also provided for aligning optics of a beam transmissometer. The method determines an offset and a rotation of a retroreflector housing that causes an optical beam to be centered.

27 Claims, 35 Drawing Sheets

$\Theta_D = \Theta_A = \tan^{-1}(r/f)$

EXPENDABLE BEAM TRANSMISSOMETER

This application claims priority to provisional U.S. Application Ser. No. 60/351,351 ("Expendable Beam Transmissometer"), filed Jan. 25, 2002.

FIELD OF THE INVENTION

The present invention relates to beam transmissometers.

BACKGROUND OF THE INVENTION

When light is projected from an underwater object to an underwater imaging device (i.e. camera or human eye), the light is either attenuated (in the form of absorption and scatter), or transmitted directly to the imaging device without perturbation. Since an image is formed only by light traveling in a straight line from object to imager, the light that is transmitted directly is called image-forming light. Light that is absorbed or backscattered never reaches the imager, and light that is forward-scattered into the imager tends only to blur or saturate the image rather than enhance it. Since the purpose of a transmissometer is to measure only the image forming light over a specified path between a light source and receiver, it is the sensor of choice for imaging system performance assessment.

The conceptual design of a transmissometer is basic. An ideal transmissometer 100 is shown in FIG. 1 according to prior art. Ideal transmissometer 100 creates a collimated beam 101 and measures the amount of collimated light (i.e. image forming light) that is received over a finite path length. A point source 103 is projected onto an objective lens 105 to form collimated beam 101. Beam 101 is projected over a finite path length of water. A second objective lens 107 is used to image collimated beam 101 to a point 109 on a light detector (if a laser is used as the light source, there is no need for the lenses). Transmissometer 100 is ideal because it creates a perfectly collimated beam with an ideal point source, and measures only the unperturbed image forming light with an ideal point receiver that has a zero acceptance angle.

Since real transmissometers cannot have ideal point sources and ideal point receivers, some of the forward-scattered light from particles in the measurement path will reach the detector and "cloud" the measurement. The problem with real transmissometers is twofold. First, an ideal point source cannot be achieved, thereby producing some divergence angle to the collimated beam. Second, an ideal point receiver cannot be achieved, thereby producing some finite acceptance angle for light entering the receiver.

In order to overcome these limitations, the optical design of a real transmissometer should be assessed carefully to optimize its performance and limit its cost. Typically, one of two optical design approaches can be taken for a real transmissometer. The first is the "cylindrically limited beam" approach (CLB), and the second is the "diverging collimated beam" approach (DCB).

A CLB transmissometer 200 is shown in FIG. 2 according to prior art. It consists of a projector, a measurement cylinder (or path), and a receiver. A light source 217 (i.e. LED) is placed behind a field stop 205 in a projector 201. An objective lens 203 is used to image field stop 205 at the receiver entrance aperture, where a second objective lens 207 is placed. A receiver field stop 209 is sized and placed in front of a light detector 211 (i.e. photodiode) such that the apparent position of the projector aperture in water is imaged within the boundaries of receiver field stop 209. The defining feature of this type of instrument is that a lossless cylindrical beam is created between objective lens 203 of projector 201 and objective lens 207 of a receiver 213. Projector and receiver apertures are the same size, allowing for very long path lengths to be implemented, if necessary. The greatest angle a ray can be deviated and still be accepted by this type of system is indicated by an angle $\theta_S$ 215 in FIG. 2. Angle 215 is specified by the ratio of the beam diameter to one half the beam length. It is this ratio of beam diameter (or beam radius) to beam length that determines the percentage error of the instrument (i.e. the greater the radius to length ratio, the more forward scattered light that is accepted by receiver 215).

FIG. 3 shows a diverging collimated beam (DCB) transmissometer 300 according to prior art. It consists of a projector 301, a measurement cylinder 303 (or path), and a receiver 305. Projector 301 and receiver 305 elements are the similar as CLB transmissometer 200, but with transmissometer 300, projector and receiver field stops 307 and 309 are placed on the focal planes of projector objective and receiver objective lenses 311 and 313, respectively. This instrument type truly attempts to mimic the ideal transmissometer by providing a point source at projector 301 and a point detector at receiver 305. Since there is divergence out of projector 301, the receiver aperture should be larger than the projector's aperture. Performance of this type of transmissometer is not based on the radius to length ratio, but rather on how well it can mimic the ideal transmissometer with a point source and receiver.

Beam transmissometers are typically expensive scientific-grade instruments. However, a beam transmissometer is often used in applications in which the beam transmissometer is not easily retrievable after the completion of the application. (One example is the determination of a beam attenuation coefficient of seawater by launching a probe from a submarine.) Thus, there is a real need for providing a high quality beam transmissometer that may be inexpensively manufactured in order to be expendable if needed.

BRIEF SUMMARY OF THE INVENTION

The present invention provides apparatus for a beam transmissometer. In an embodiment of the invention, the beam transmissometer includes a light emitting diode (LED) that emits green or blue light, collimating apparatus including an objective lens to form a projected optical beam, a retroreflector that directs the projected beam, imaging apparatus that directs the beam onto a detector that converts the projected beam into an electrical signal, and signal processing circuitry that enhances the reception of the optical beam. In the embodiment, the LED signal source is modulated in a pulsed fashion so that the effect of reflections of the beam along its traversed path is ameliorated. Signal processing circuitry amplifies, filters, and synchronizes to the electrical signal. In the embodiment, a calculating unit uses the processed signal to determine a beam attenuation coefficient, which is indicative of the visibility of a medium (e.g. seawater) in which the transmissometer is immersed. In some applications of the embodiment, the beam transmissometer may be expendable if retrieval of the transmissometer is not desirable in accordance with the cost and difficulty of retrieving the transmissometer. However, there may be other applications in which the transmissometer may not be deemed to be expendable and thus the transmissometer may be retrieved for subsequent usage.

With another aspect of the invention, a method is provided for aligning optics of a beam transmissometer. The method determines an offset and a rotation of a retroreflector housing that causes an optical beam to be centered.

BRIEF DESCRIPTION OF THE DRAWINGS

A more complete understanding of the present invention and the advantages thereof may be acquired by referring to the following description in consideration of the accompanying drawings, in which like reference numbers indicate like features and wherein.

DETAILED DESCRIPTION OF THE INVENTION

In the following description of the various embodiments, reference is made to the accompanying drawings which form a part hereof, and in which is shown by way of illustration various embodiments in which the invention may be practiced. It is to be understood that other embodiments may be utilized and structural and functional modifications may be made without departing from the scope of the present invention.

The sensor can be divided into three subsystems: the optical subsystem, the electrical subsystem, and the mechanical subsystem. (An optical frequency spectrum is typically the electromagnetic spectrum within the wavelength region extending from ultra-violet at approximately 1 nm to far infrared at approximately 0.1 mm. The optical frequency spectrum includes electromagnetic radiation visible to a human eye as well as electromagnetic radiation between the shortest wavelengths associated with radio transmission and the longest wavelengths associated with X-rays.) The optical subsystem contains a projector, measurement cylinder, and receiver elements. The electrical subsystem contains a light emitting diode (LED) driver (which includes an LED output stabilization circuit), receiver electronics (photodiode signal amplifier and data transmission circuitry), and a power supply circuit (with battery power source). The mechanical subsystem contains an electro-optics housing, a combination nose/retroreflector housing, and a housing support frame.

Figure 1:
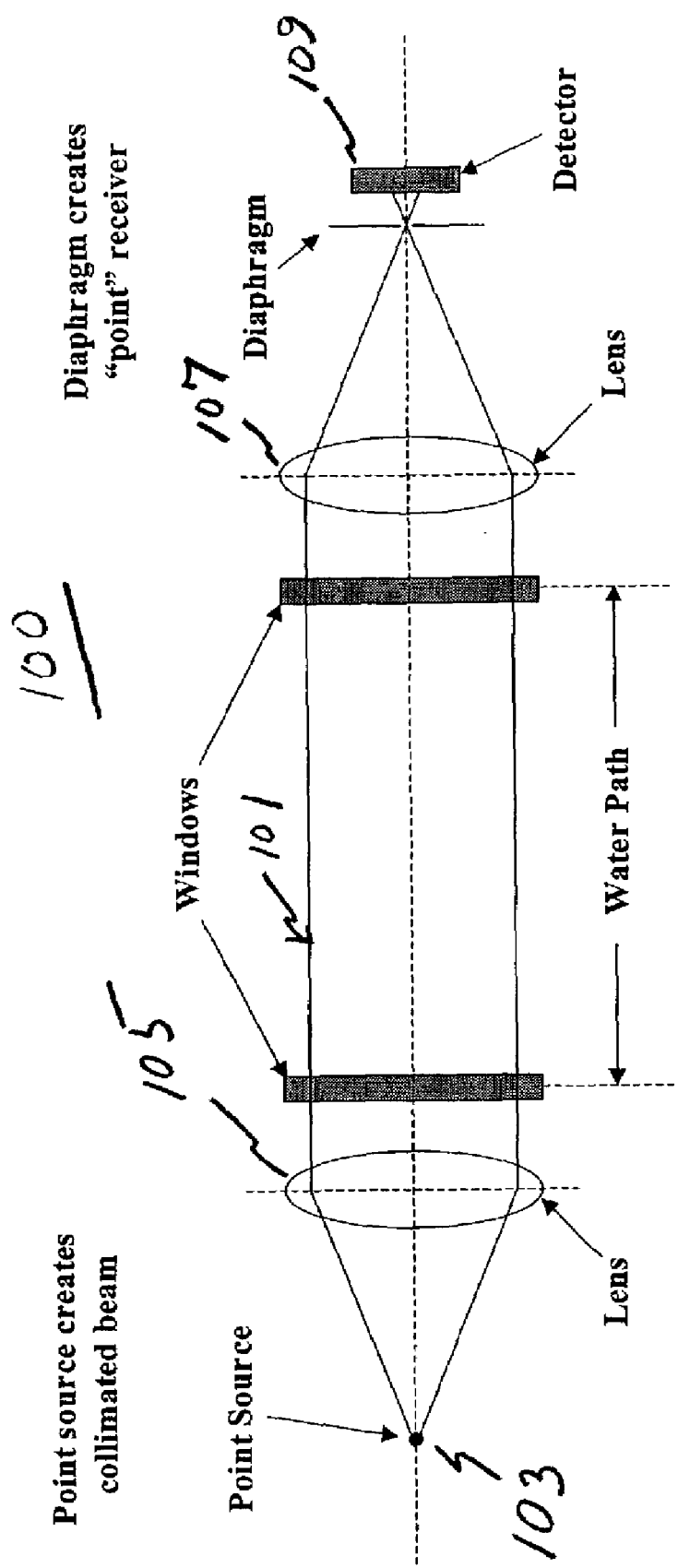
FIG. 1 shows an ideal beam transmissometer according to prior art.
Figure 2:
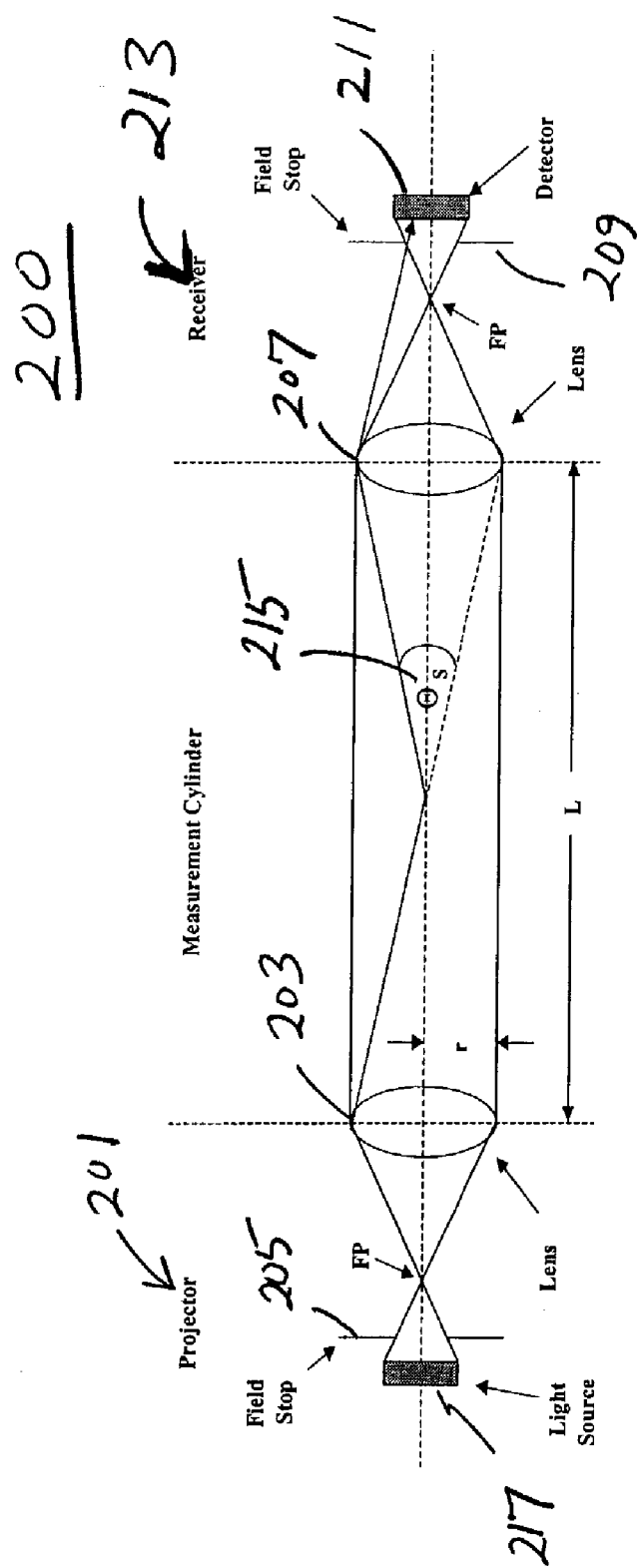
FIG. 2 shows a cylindrically limited beam (CLB) transmissometer according to prior art.
Figure 3:
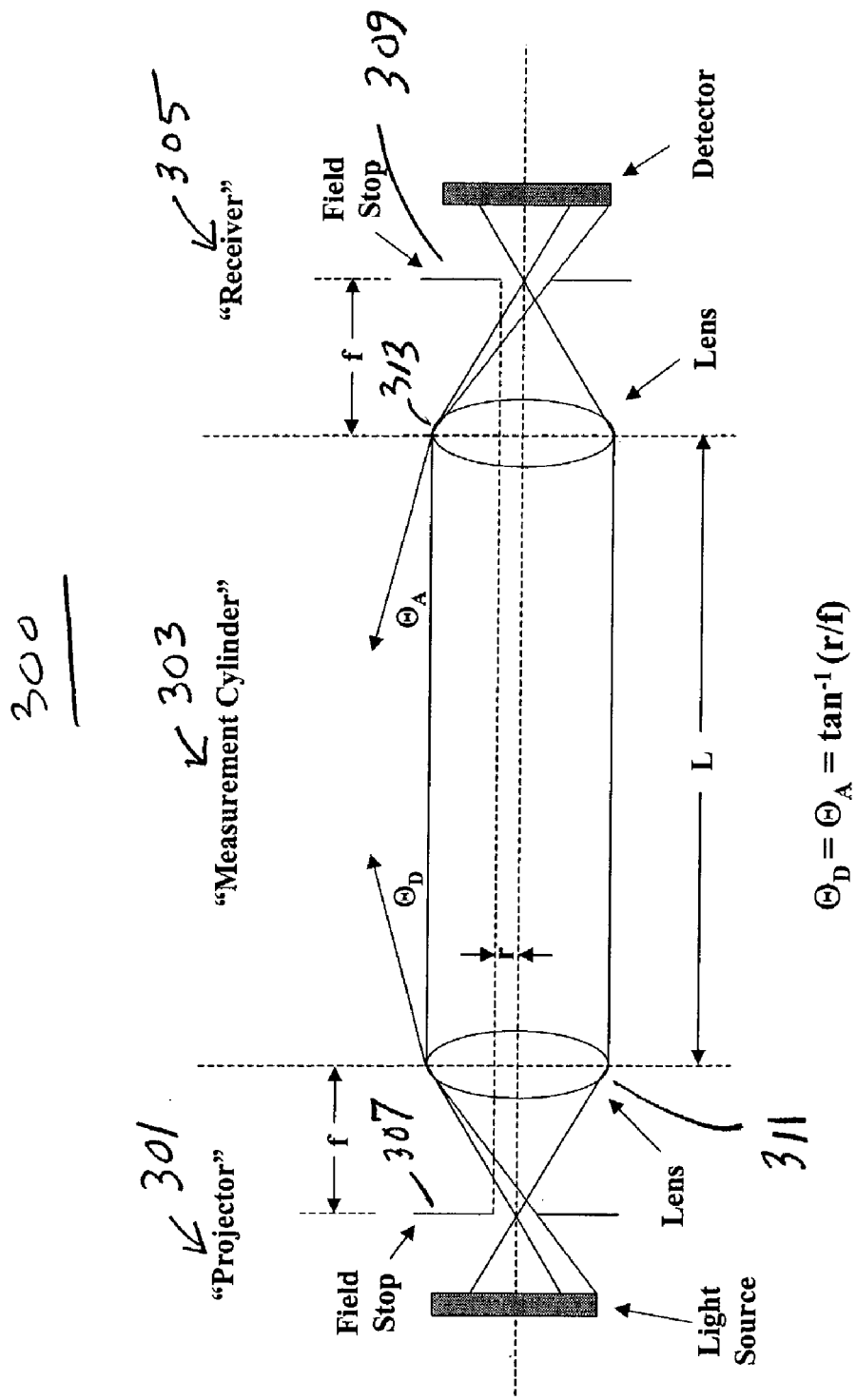
FIG. 3 shows a diverging collimated beam (DCB) transmissometer.
Figure 4:
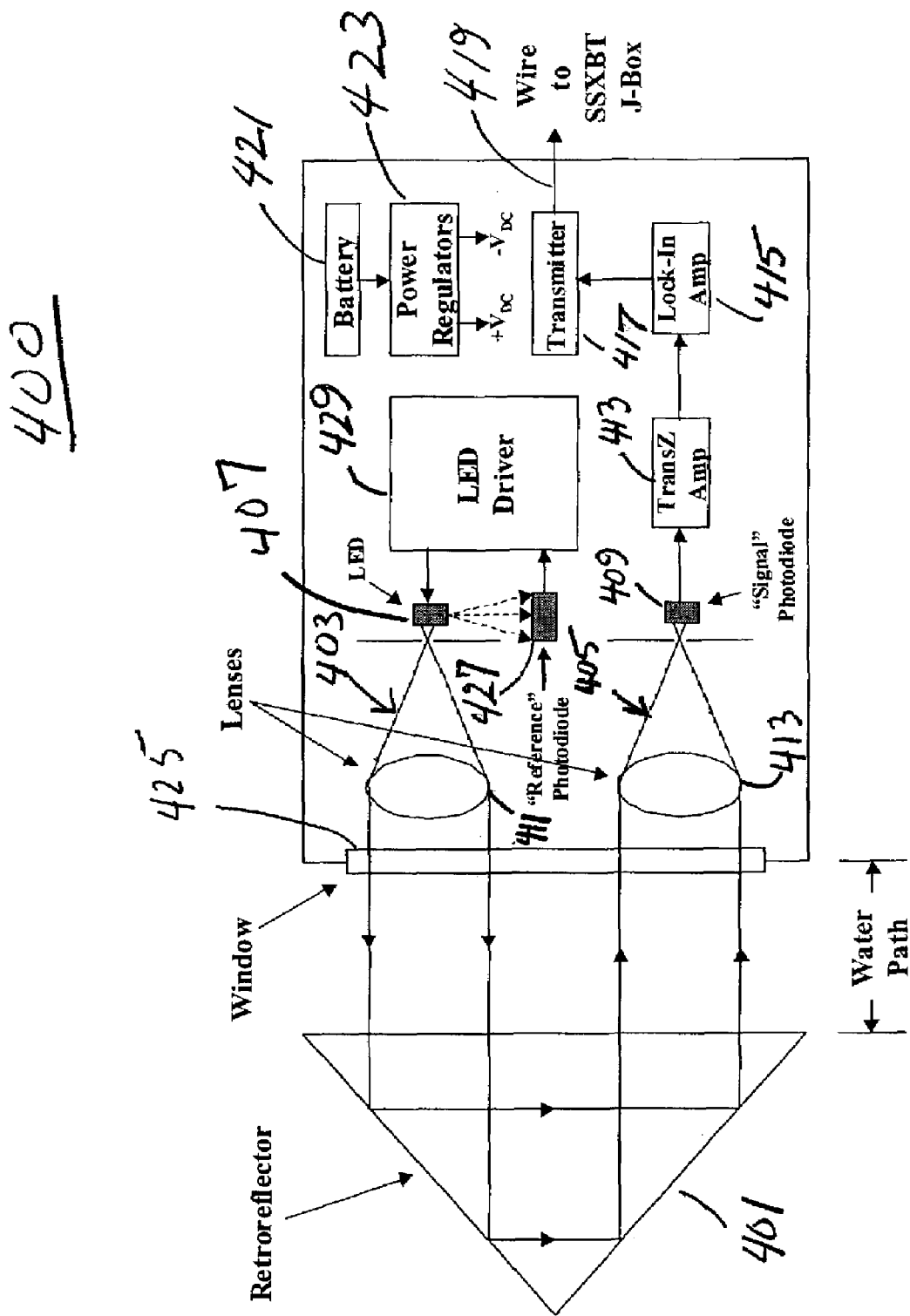
FIG. 4 shows a functional block diagram of a beam transmissometer in accordance with an embodiment of the invention.

FIG. 4 shows a functional block diagram of a beam transmissometer 400 in accordance with an embodiment of the invention. A retroreflector 401 (or corner cube) is used to fold the measurement cylinder. This folded water path occurs as the light from a projector 403 is reflected off corner cube 401 and returns to a receiver 405 located adjacent to projector 403. Retroreflector 401 essentially doubles the optical path length without doubling the size of the instrument and places all of the components (with the exception of retroreflector 401) in one housing, allowing for ease of manufacture and alignment.

The optical section comprises all of the sensor optical elements from an LED light source 407 to a receiving photodiode light detector 409. The elements are designed and configured to model the aforementioned diverging collimated beam (DCB) style transmissometer. However, other embodiments of the invention may use other approaches for imaging an optical beam such as a "cylindrically limited beam" approach (CLB). A point source is created with a super-bright green (or blue) LED and two small apertures (the second aperture approximates the point source). The point source is then collimated with a projector's objective lens 411 and another aperture, and the collimated beam is projected into the measurement volume. At receiver 405, the collimated, image forming light from the projector is then received through a fourth aperture and reduced back to a point via a condensing lens 413. (In other embodiments of the invention, another type of light source, e.g. a laser, may be utilized. With a laser signal source, lens may not be necessitated.) This point of received light is fed through a fifth aperture (approximating a point receiver) where it strikes photodiode light detector 409 (a bandpass optical filter is placed in front of photodiode 409 to eliminate undesirable out-of-band light). Photodiode 409 converts the incident light flux to an output current.

The electrical section completes the loop from projector 403 to receiver 405 in an electrical sense. An LED driver circuit 429 (as discussed in the context of FIG. 13) generates a pulse that is transmitted to LED light source 407. LED 407 is pulsed/modulated at a rate of approximately 100–500 Hz, and a closed loop stabilization circuit is incorporated to maintain a constant LED output flux while LED 407 is being modulated. (In other embodiments of the invention, LED light source 407 may be pulsed in an aperiodic fashion.) The receiver circuit comprises a photodiode transimpedance amplifier 413, a lock-in amplifier 415, and a data transmission circuit 417. Transimpedance amplifier 413 acts to convert the input photodiode current to a voltage and isolate the photodiode signal from the rest of the electronics. Lock-in amplifier 415 acts to synchronously detect (in frequency and in phase) the amplifier's output signal with the LED's chopper rate. Data transmission circuit 417 converts the lock-in amplifier's DC level output to a differential digital pulse train for transmission over the a wire 419. The last component of the electrical section is a power supply circuit, which contains a battery 421 and a charge-pump and switching regulator/linear post-regulator 423. The power supply provides the traditional complementary supply rails (e.g. +/−12 volts) for the analog circuitry, and the traditional +5 volts for the digital circuitry.

Optical Subsystem Design

The optical section is comprised of the following components:
1. An LED
2. Two lenses
3. A retroreflector
4. A window
5. A photodiode (with included bandpass filter)

An LED, an objective lens, and three apertures comprise the projector. A retroreflector creates the folded water path. A second lens, photodiode, and two more apertures comprise the receiver. A window 425 (as shown in FIG. 4) is used to seal the optical components (with the exception of the retroreflector) from seawater without appreciable degradation to the instrument's light path. The optical components and a description of each are given in Table 1 as shown below.

TABLE 1

Optical Component Description

| Component | Size | Description |
| --- | --- | --- |
| LED | φ5 mm | Green, wavelength = 525 nm |
| | | Light intensity - 7000 millicandelas (mcd) |
| | | Emission angle = 15° |
| Lenses | φ6 mm | Effective focal lengths = 36 mm (projector), |
| | | 50 mm (receiver) |
| | | Anti-reflection coating |
| | | ≧95% optical transmission (2 way) |
| Retroreflector | φ12.7 mm | Silver coated to increase reflection |
| | | >80% reflection (2 way) |
| Photodiode | Effective sensitive area = 3.7 × 3.7 mm$^2$ | Monochromatic silicon photodiode |
| | | Integral optical bandpass filter @ 520 nm |
| | | Junction capacitance = 600 pF |
| | | Noise equivalent power = 7 × 10$^{-15}$ W/Hz$^{1/2}$ |
| Borosilicate Window | φ20 mm × 3 mm | ≧80% optical transmission (2 way) |

The embodiment of the invention uses a green LED to support a coastal water environment application. A blue LED may also be used in place of the green LED to support an open ocean water environment. The calculations that follow are largely based on specified device parameters, although some parameters are estimated (e.g. diffuser loss and diffuser image smearing effects).

Figure 5:
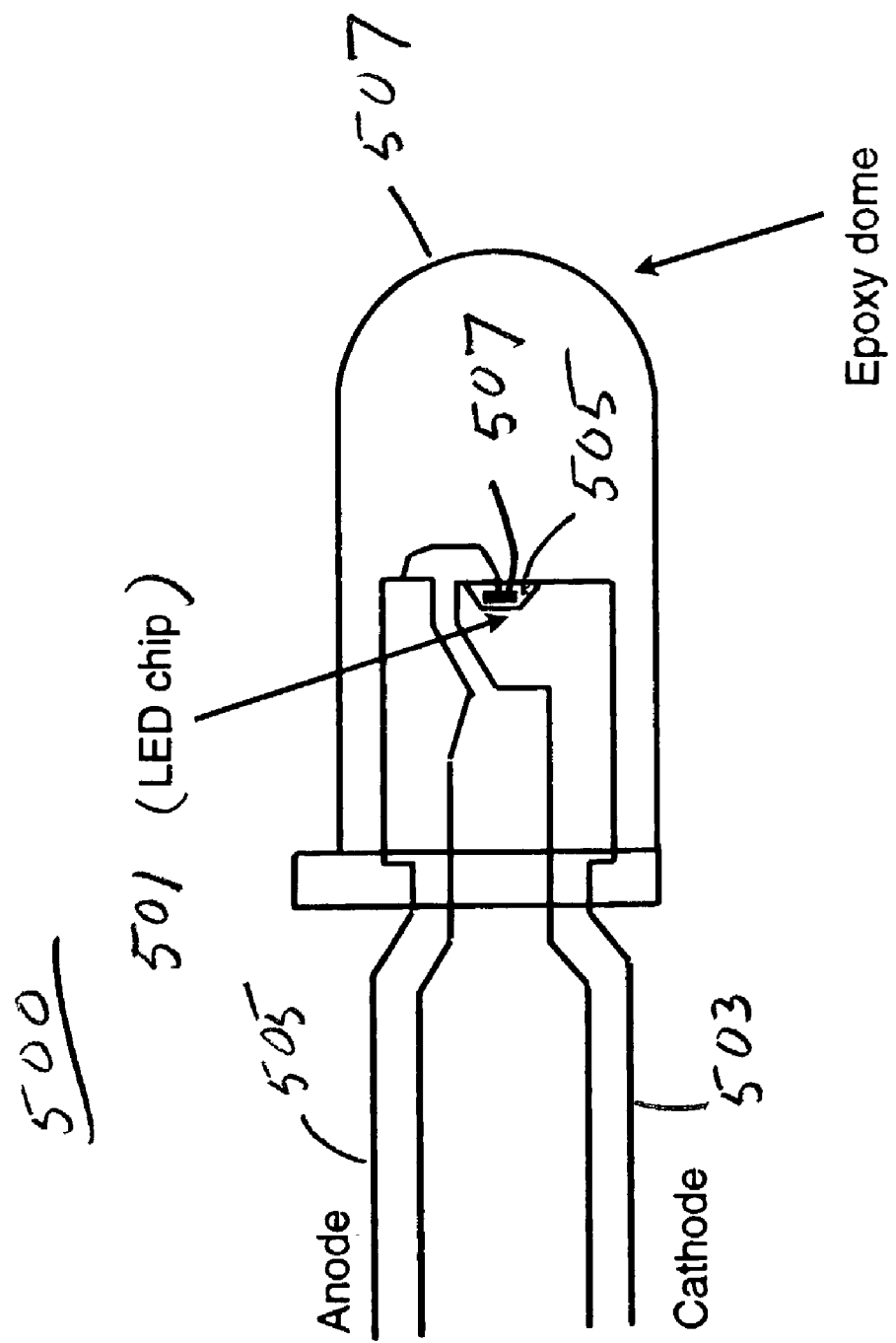
FIG. 5 shows a construction of a light emitting diode in accordance with an embodiment of the invention.

The projector comprises an LED, a point source, and a collimator. The LED is the light source for the transmissometer. The point source component approximates the desired point source that defines the performance of the transmitter element of a DCB transmissometer. The collimator performs the collimation of the light emitted from the point source and projection into the measurement path or volume. FIG. 5 shows a construction of a light emitting diode 500. An LED chip 501 is placed in a reflecting cavity within a cathode terminal 503. A cathode 505 of LED chip 501 is bonded directly to the base of the reflecting cavity of cathode terminal 503. A wire is bonded to an anode 507 of LED chip 501 and the wire is fed over to anode terminal 505. The epoxy dome forms a lens that forms the beam pattern (or emission angle) for LED 500. Light is directly emitted out of LED 500 through the top of LED chip 501, while light is indirectly emitted (via reflection) by the reflecting cavity from the sides of LED chip 501.

Figure 6:
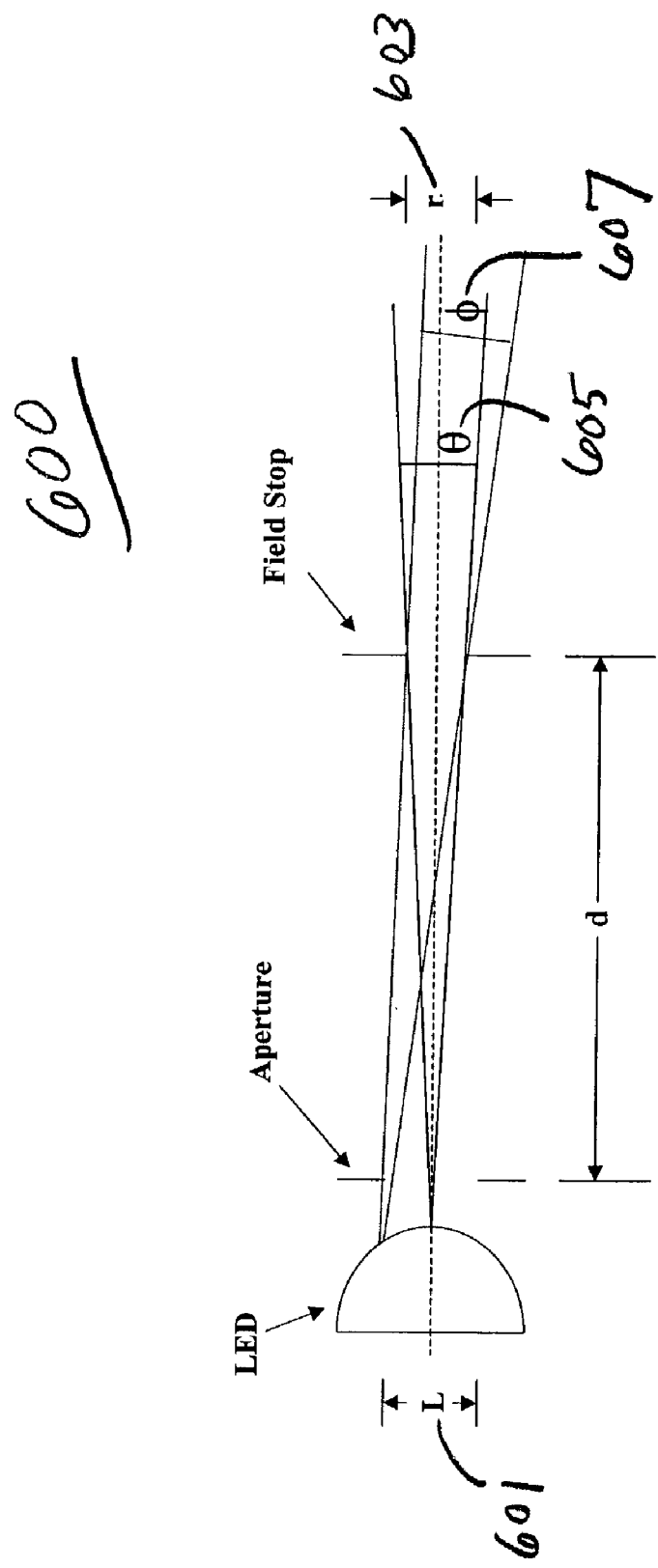
FIG. 6 shows a point source optical diagram in accordance with an embodiment of the invention.

In the embodiment, LED 500 has a peak intensity of 7000 mcd at a peak wavelength of 525 nm, and an emission angle of 15 degrees. The wire bonding within the LED housing is similar to FIG. 5, except that a second cathode wire is bonded to the LED chip rather than directly to the reflecting cavity. Both of the wire bonds (anode and cathode) are made on top of the LED chip. FIG. 6 shows a point source optical diagram in accordance with an embodiment of the invention. A point source is created with the LED and two apertures (one with diameter=L=1.6 mm, corresponding to a diameter 601, and a second with diameter=r=0.2 mm, corresponding to a diameter 603). The first aperture is approximately 1.6 mm to provide a reasonable beam diameter out of the collimator given the space constraints of the projector. The LED's light output is passed through the larger aperture, which is used to limit the angular extent of the light output. The output of the larger aperture is then passed into the smaller point source aperture. This aperture is placed at a substantial distance from the first aperture (d=24 mm). Since L<<d, the angles θ 605 and φ 607 shown as shown in FIG. 6 are essentially the same which means that the intensity of light passing through the smaller aperture approximates a point source.

Because the dual wire bonds on top of the LED chip generate a very patchy, non-uniform beam, a simple diffuser element was placed in front of the larger aperture. The diffused beam generated is quite uniform, although attenuated in its intensity. The diffuser also acts to smear or average the beam intensity. Diffuser attenuation, coupled with the smearing effect, was estimated to reduce the point source intensity by approximately two orders of magnitude. (The first order of magnitude for the translation of peak LED intensity to average LED intensity, and the second order of magnitude for the attenuation through the diffuser.)

Figure 7:
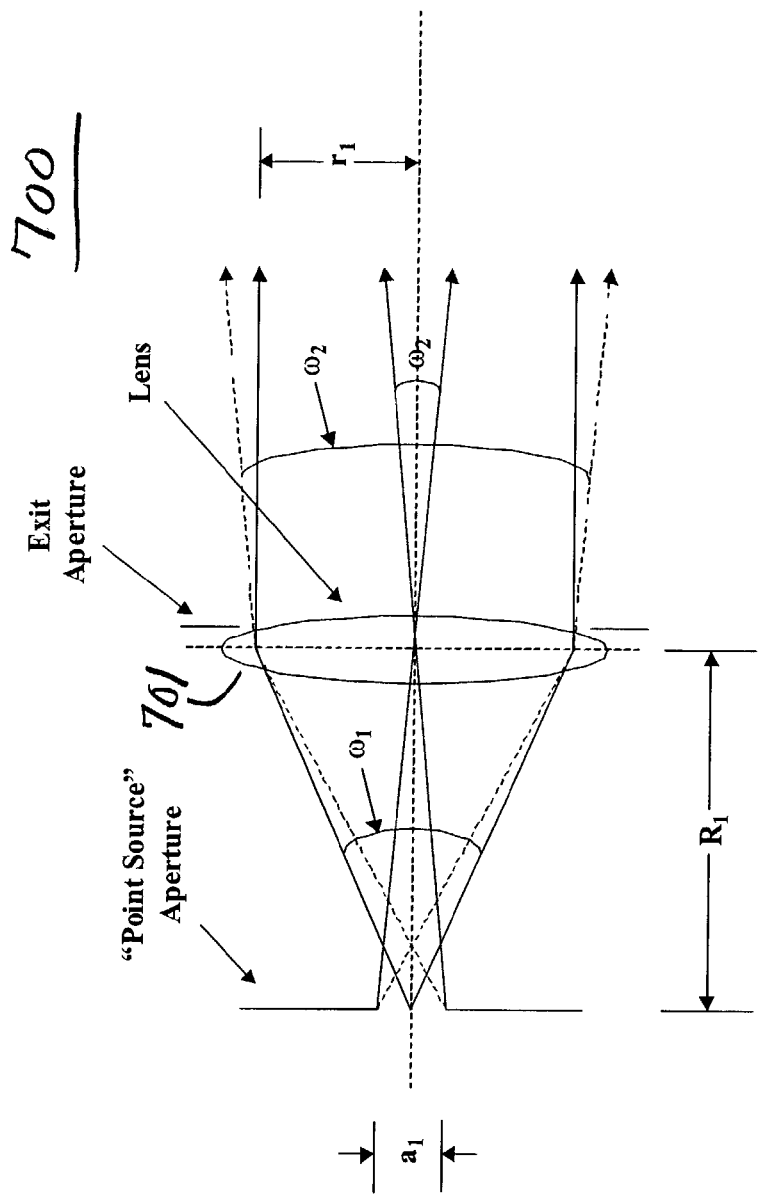
FIG. 7 shows a diagram of a collimator in accordance with an embodiment of the invention.
Figure 8:
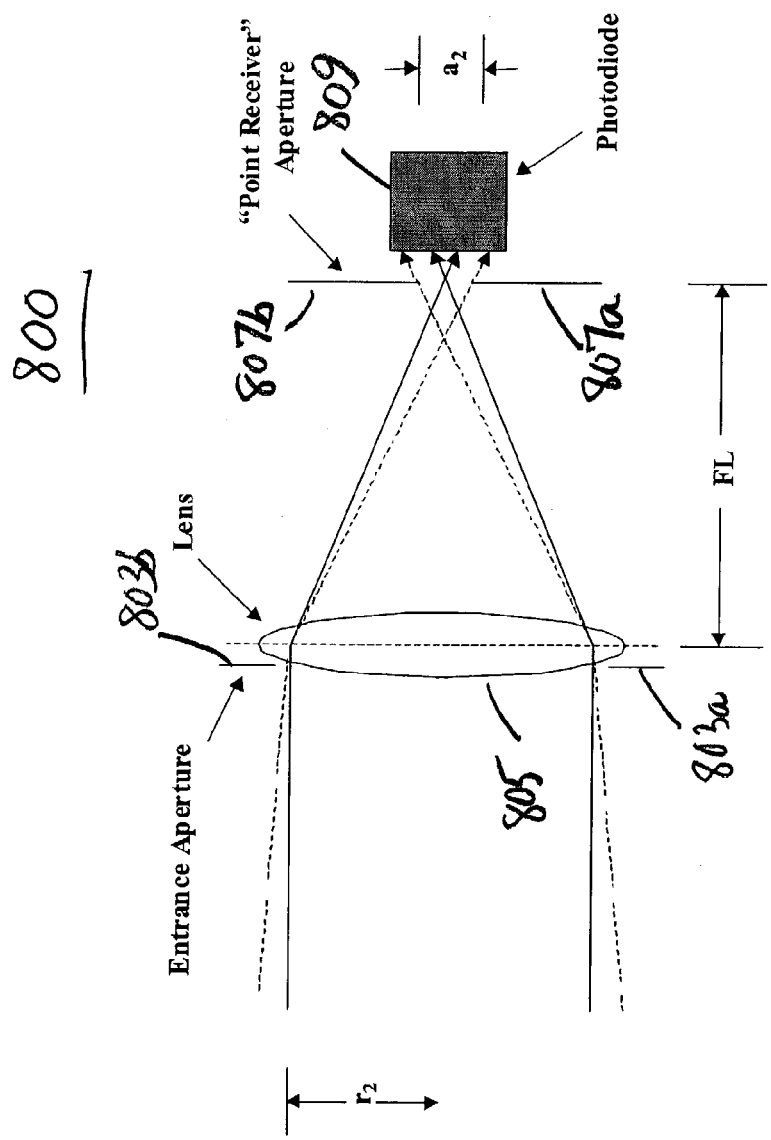
FIG. 8 shows a receiver optical diagram in accordance with an embodiment of the invention.

FIG. 7 shows a diagram of a collimator 700. The point source aperture output is collimated by the objective lens 701. A final aperture is placed in front of the lens to limit beam diameter and to block any stray light out of the projector. Since the focal length of the lens is 36 mm and the aforementioned L/d ratio for the point source is 1:15, the beam diameter for the collimated beam out of the lens is 2.8 mm. The projector aperture in front of the lens is therefore set to have a diameter of 2.8 mm. The parameters shown in the figure are:
- $\omega_1$=solid angle of point source (steradians)
- $\omega_2$=solid angle of projector (steradians)
- a=point source aperture=0.2 mm
- r=projector beam radius=1.4 mm
- $R_1$=lens focal length=36 mm FIG. 8 shows a receiver optical diagram. A receiver 800 is comprised of an entrance aperture 803*a* and 803*b*, a converging lens 805, a point receiver aperture 807*a* and 807*b*, and a photodiode 809. Entrance aperture 803*a* and 803*b* limits external stray light from entering receiver 800, and sets the target for alignment and sizing of the measurement beam. The lens 805 is used to reduce the incoming collimated beam to a point, which is represented by the point receiver aperture. Point receiver aperture 807*a* and 807*b* approximates the desired point receiver that defines the performance of the receiver element of a DCB transmissometer. Light transmitted through this aperture impinges on the face of photodiode 809. A 520 nm bandpass filter is located on the face of the photodiode, with the sensitive photodiode surface recessed within the photodiode housing.

The embodiment of the invention uses a green LED for a coastal water environment application. A blue LED may also be used in place of the green LED to support an open ocean water environment. (However, other embodiments of the invention may use optical beams having different wavelengths.) The calculations that follow are largely based on specified device parameters, although some parameters are estimated (e.g. diffuser loss and diffuser image smearing effects). The purpose of the radiometry calculations was not to obtain exact solutions, but to obtain an estimate so that the chosen optical elements could produce a beam to provide a reasonable receiver spot size and a sufficient electrical signal out of the receiving photodiode. The receiver spot size should be optimized to maximize measurement beam diameter through the water, while still allowing for ease of beam alignment within the selected target provided by the aperture. Given the chosen projector elements detailed in section, a spot size calculation follows using the defined parameters detailed in section, and the following:
- $I_1$=average point source intensity=50 mcd=0.05 lm/ster
- $A_1$=lens area subtended by $\omega_1$ (mm²)
- $A_2$=point source aperture area subtended by $\omega_2$ (mm²)
- F=light flux at lens (lumens)
- PL=path length=500 mm, Determining $\omega_1$, $$\omega_1 = A_1/R_1^2 = \pi(1.4 \text{ mm})^2/(36 \text{ mm})^2 = 4.75 \times 10^{-3} \text{ ster}$$

Determining $\omega^2$, $$\omega_2 = A_2/R_1^2 = \pi(0.1 \text{ mm})^2/(36 \text{ mm})^2 = 2.42 \times 10^{-5} \text{ ster}$$

Defining $A_3$=projected area at the receiver $$A_3 = \omega_2 R_2^2,$$

where $R_2$=solid angle radius for $\omega_2$ projected on receiver $$R_2 = R_0 + PL,$$

where $R_0$=solid angle radius for $\omega_2$ projected on collimator lens

Determining $R_0$, $$R_0 = (A_1/\omega_2)^{0.5} = 504.42 \text{ mm}$$

Therefore, $$R_2 = 504.42 \text{ mm} + 500 \text{ mm} = 1004.42 \text{ mm}$$

And, $$A_3 = 24.41 \text{ mm}^2 \rightarrow \text{beam radius at receiver} = 2.78 \text{ mm}$$

The beam diameter at the receiver will then be 5.56 mm. Since the receiver's cylindrical bore size dictates the use of a ¼ inch (6.35 mm) lens, this constrains the flexibility in alignment of the beam. To alleviate this constraint, the projector aperture diameter is reduced from 2.8 mm to 2 mm that reduces the beam diameter at the receiver to approximately 4 mm, allowing plenty of room to focus on the aperture target during beam alignment. The receiver signal output calculations begin with the flux output from the projector and use the specified transmission parameters for each of the optical components to calculate a final flux on the receiver's photodiode sensitive area. Determining F (with 2 mm projector aperture diameter), $$\omega_1' = \omega_1(2/2.8)^2 = \mathbf{0.51\omega_1}$$

$$F = I_1\omega_1' = (0.05 \text{ lm/ster})(2.42 \times 10^{-3} \text{ ster}) = 1.21 \times 10^{-4} \text{ lm}$$

Using transmission through optics→$T_{lenses}$=0.9, $T_{window}$=0.8, and $T_{corner\ cube}$=0.8, $$T_{optics} = T_{lenses} T_{window} T_{corner\ cube} = 0.58$$

Determine flux at receiver detector ($F_{det}$), $$F_{det}=FT_{optics}=7.02\times10^{-5} \text{ lm}$$

And converting to watts (using conversion factor 685 lm/W), $$F_{det}=0.1 \text{ } uW=1\times10^{-7} \text{ } W$$

In the embodiment, the photodiode is used in conjunction with a 520 nm bandpass filter and has a noise equivalent power (NEP) of $7\times10^{-15}$ W/Hz$^{1/2}$. Since the equivalent bandwidth of the receiver lock-in amplifier's low pass filter is typically on the order of 10 Hz, the NEP over the measurement bandwidth is $7\times10^{-14}$ W. Because the receiver implements a synchronous detection mechanism (or lock-in amplifier) in its electronics section that is theoretically capable of detecting a signal down to the photodiode's NEP, $F_{det}$ is typically above the noise level of the receiver's electronics.

DCB transmissometer performance (or accuracy) is directly proportional to the sum of the projector divergence angle and the receiver acceptance angle. The sum of the angles is the maximum allowable scattering angle ($\theta_S$) that will be measured by the device. The maximum scattering angle for the existing transmissometer is 1.15°. Determining divergence angle ($\theta_d$), $$\theta_d=\tan^{-1}(r_p/f_p),$$

where $r_p$=0.1 mm=projector point source aperture radius and
$f_p$=36 mm=projector lens focal length
$\theta_d$=0.16°
Determining acceptance angle ($\theta_a$), $$\theta_a=\tan^{-1}(r_r/f_r),$$

where $r_p$=0.5 mm=projector point source aperture radius and
$f_p$=50 mm=projector lens focal length
$\theta_a$=0.57°
Therefore, $$\theta_S=\theta_d+\theta_a=0.73° \text{ and } \theta_S<1.15°$$

Electrical Subsystem Design

The electrical subsystem consists of two circuit boards and a battery. The first circuit board contains the LED driver and power supply circuitry, while the second board contains the receiver circuitry. The LED, reference photodiode, and battery all attach to the first circuit board, while the signal photodiode and signal wire attach to the second circuit board.

Figure 9:
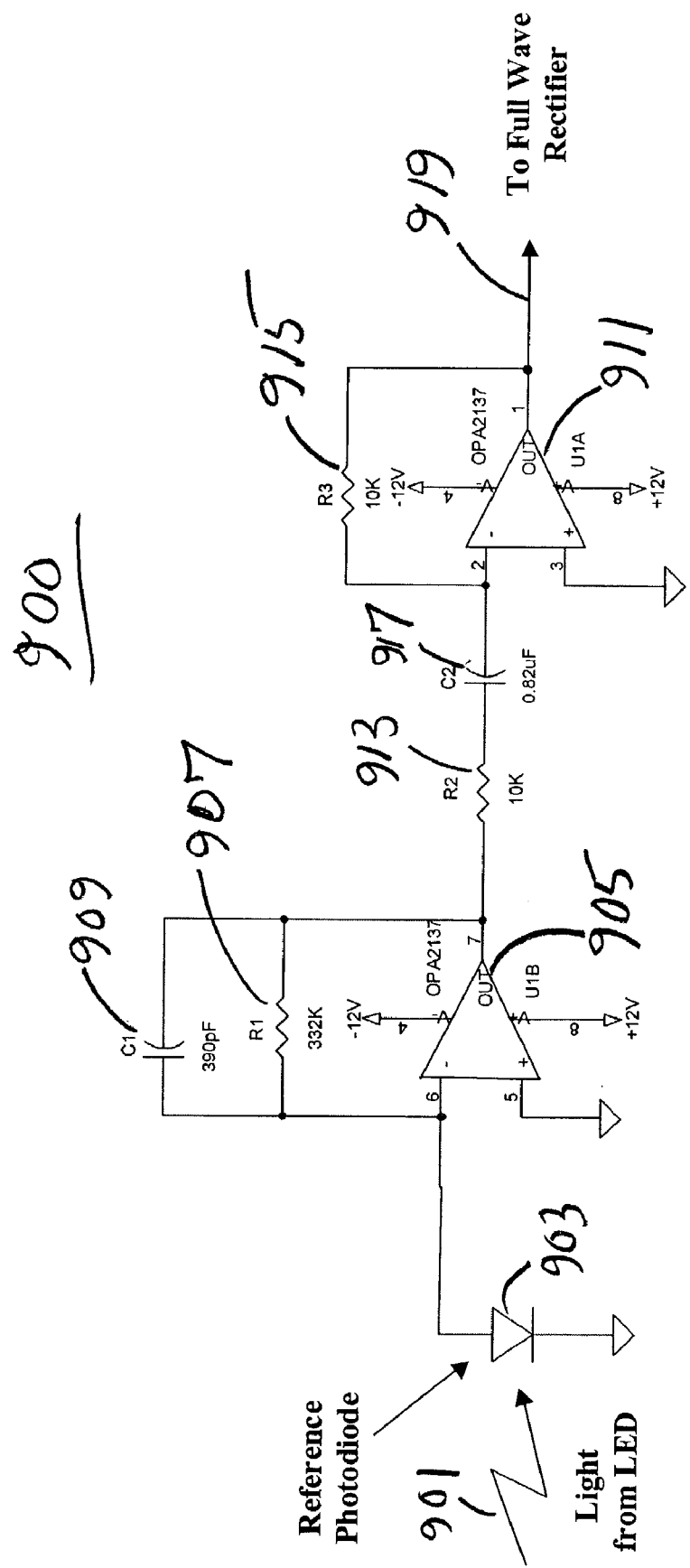
FIG. 9 shows a reference photodiode/transimpedance amplifier in accordance with an embodiment of the invention.
Figure 10:
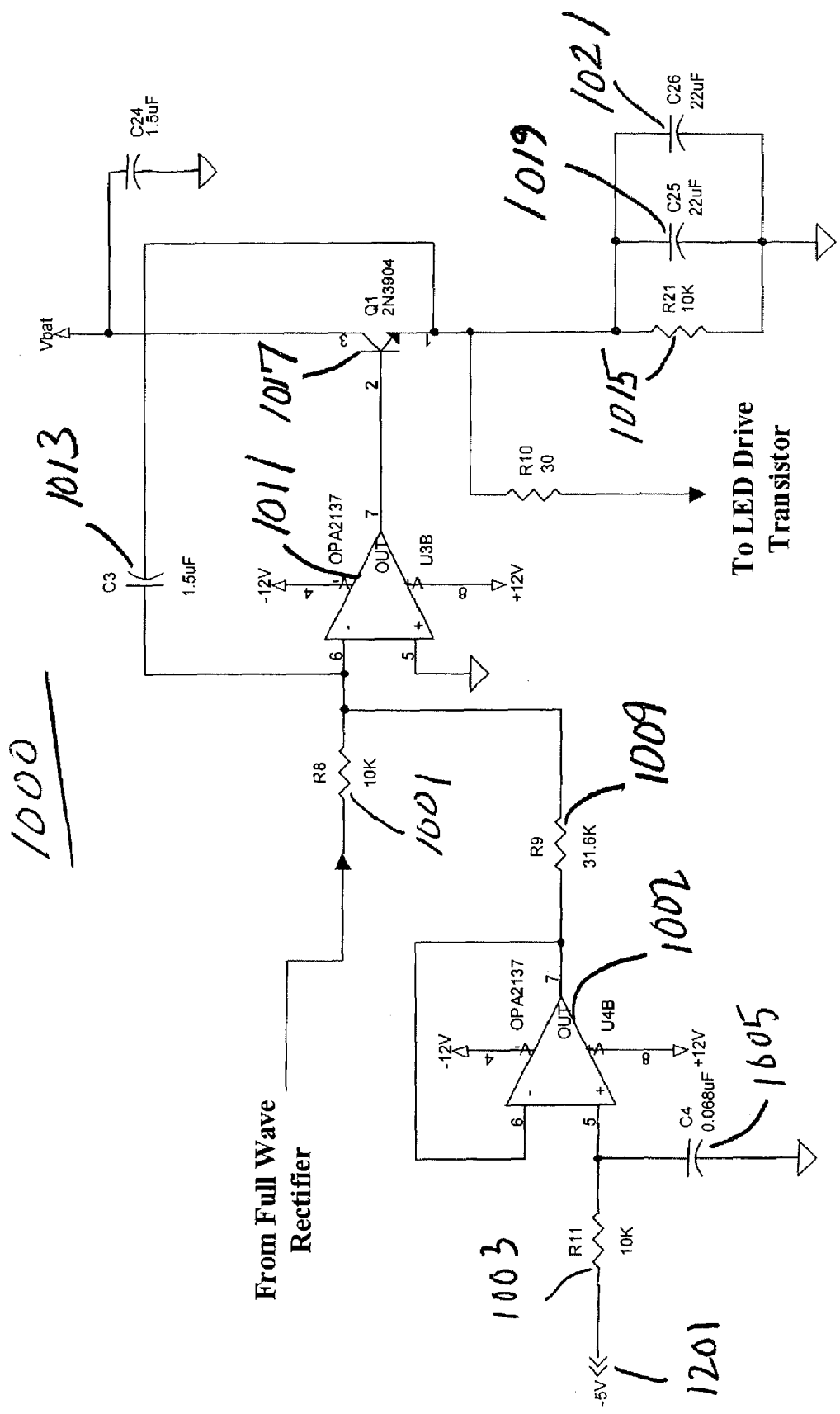
FIG. 10 shows an integrator circuit in accordance with an embodiment of the invention.
Figure 13:
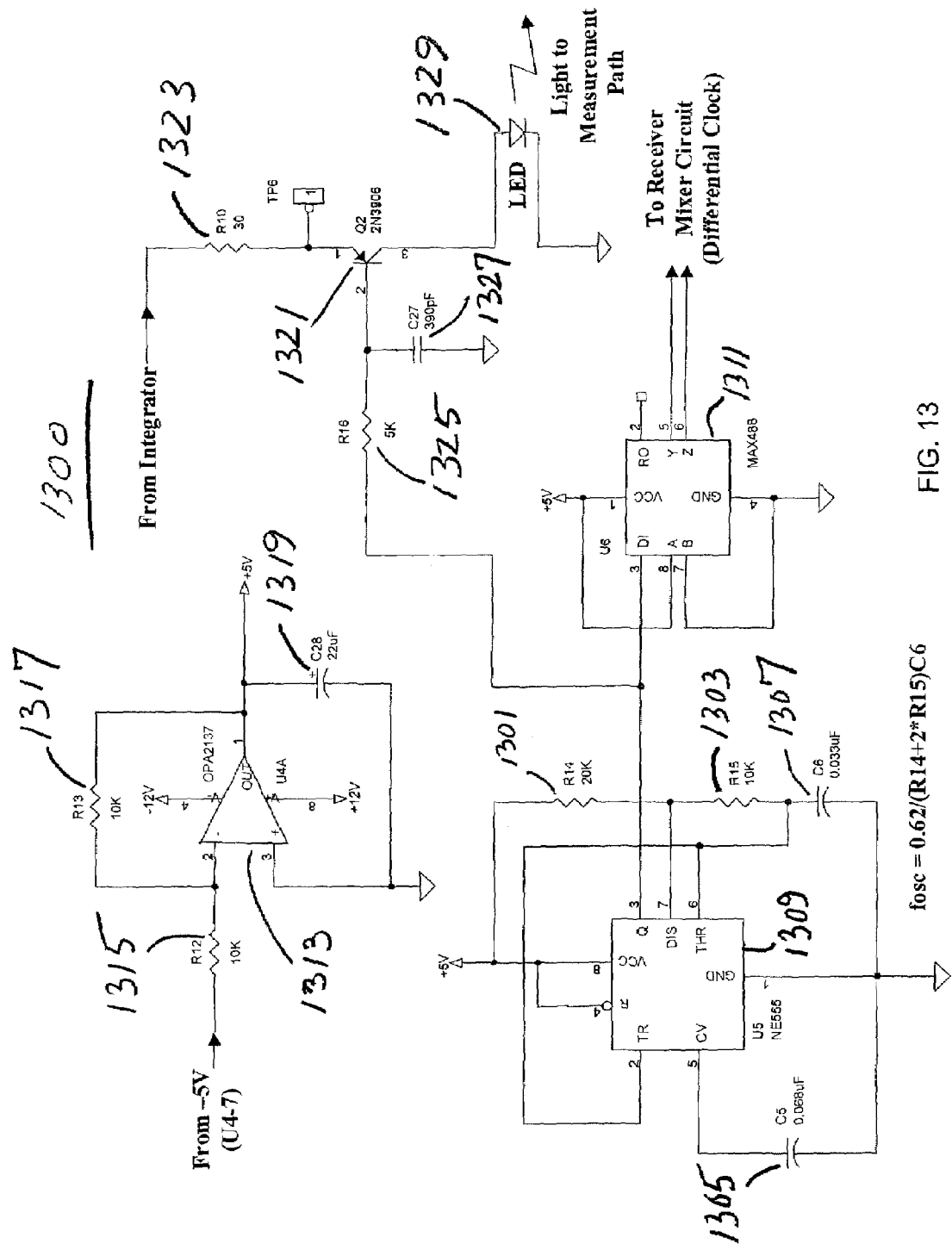
FIG. 13 shows an electrical schematic of a clock and LED driver in accordance with an embodiment of the invention.

FIG. 9 shows a reference photodiode/transimpedance amplifier 900. Within this driver and stabilization circuit, a reference photodiode/transimpedance amplifier combination monitors an LED light output 901. A pulsed voltage output of the transimpedance amplifier is then rectified to produce a DC level current that is compared with a reference current that determines the level of LED light output. This current difference is fed into an integrator 1000 (as shown in FIG. 10) whose output feeds the drive transistor for the LED. If the rectifier's output is lower than the reference signal, integrator 1000 acts to increase the drive current to the drive transistor that increases LED light output. If the rectifier's output is higher than the reference signal, integrator 1000 acts to decrease the drive current to the drive transistor that decreases LED light output. The control loop will continue to modify the drive transistor current accordingly until an equilibrium state is reached between the rectifier's output and the reference signal. This equilibrium state is defined by a constant (or zero) difference between the two signals. An LED driver consists of the circuitry as shown in FIG. 13. The LED and reference photodiode are not shown in FIG. 13, but are referred to by the "LED (+)", "LED(−)", and "REF_PD" signal descriptors.

In the embodiment, a reference photodiode 903 has a low temperature coefficient in the 500–550 nm band, visible range sensitivity (300–700 nm), and total lack of sensitivity beyond 700 nm. Reference diode 903 views the side of the LED through a small hole in the projector tube. Its main purpose is to provide an output current that is proportional to LED radiance at a steady state temperature. The exact relationship of output current to LED radiance need not be determined, but the output current should only be dependent upon LED radiance.

Referring to FIG. 9, U1B 905, R1 907, and C1 909 acts to convert the input reference photodiode current to an output voltage. Resistor R1 907 sets the gain (or transimpedance $G=R1=V_{out}/I_{in}$) while C1 909 creates a single pole (combined with R1 907) in the circuit to prevent significant "gain peaking" due to the junction capacitance of the photodiode. Amplifier circuit U1A 911, R2 913, R3 915, and C2 917 provide a one pole high-pass filter for a transimpedance output 919. Its output is an AC-coupled version of the reference photodiode current signal, which is ideal for a full-wave rectifier circuit 1100 as will be discussed.

Figure 11:
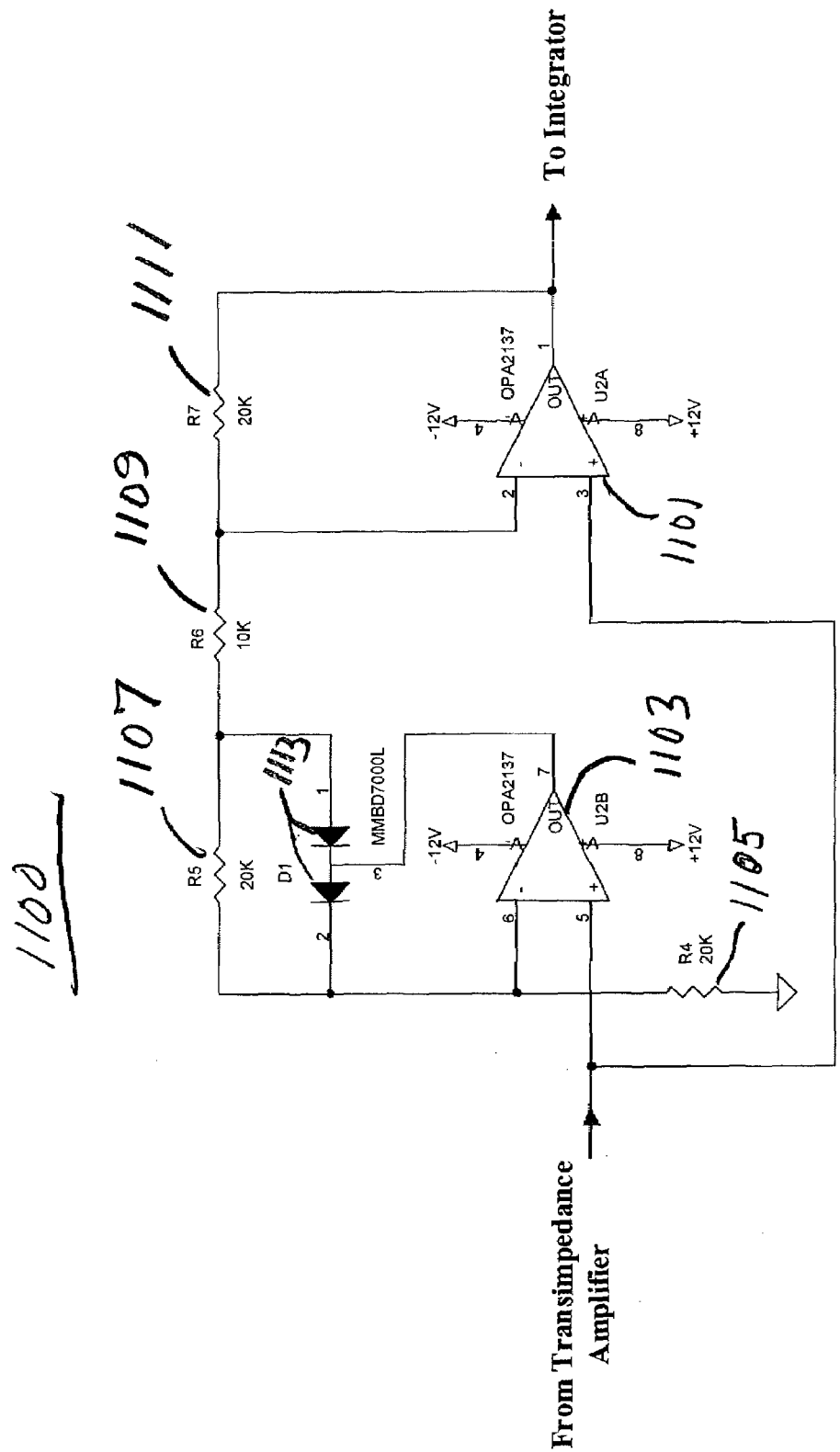
FIG. 11 shows a full-wave rectifier in accordance with an embodiment of the invention.
Figure 12:
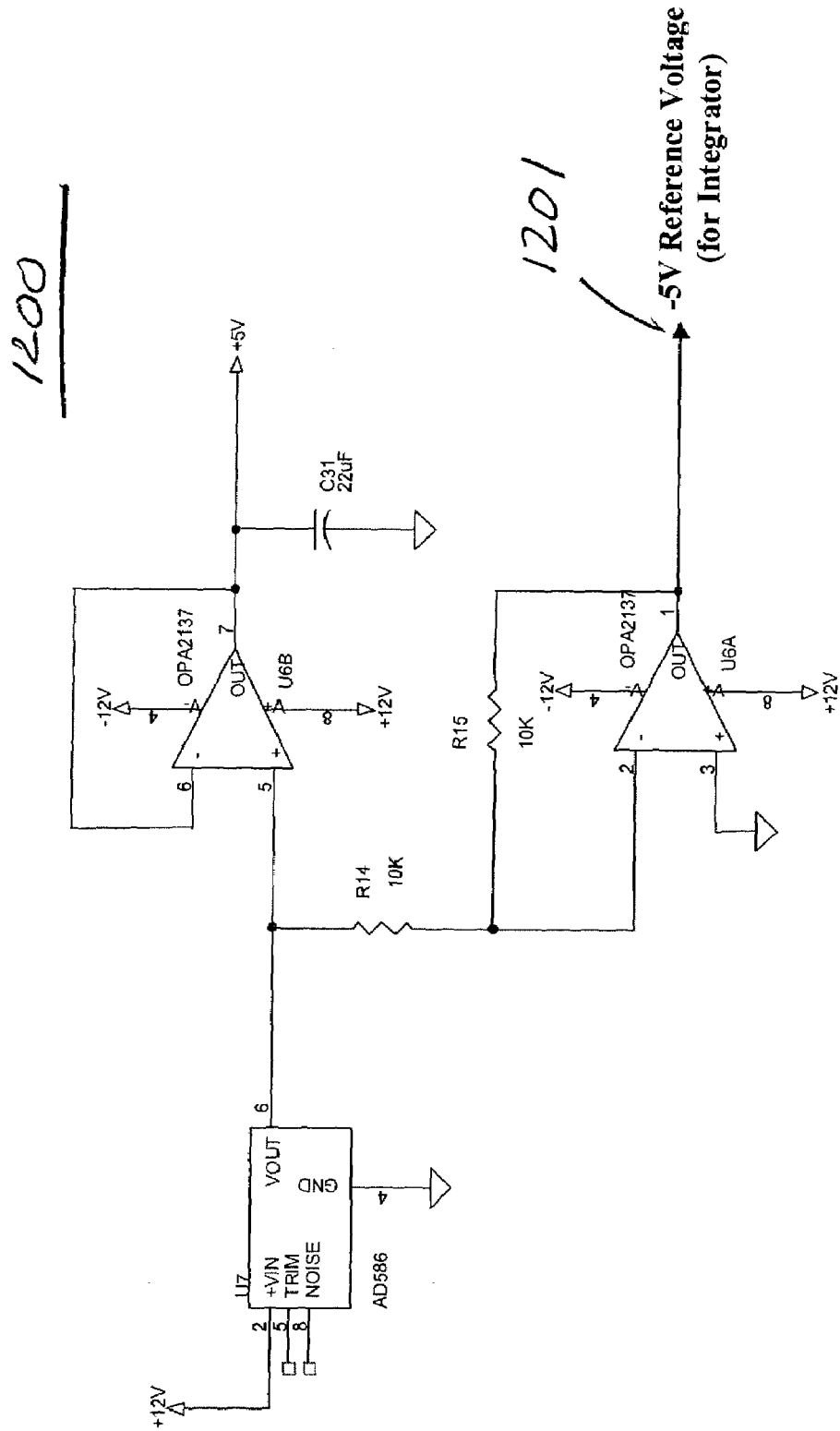
FIG. 12 shows a voltage reference circuit in accordance with an embodiment of the invention.

FIG. 11 shows full-wave rectifier 1100. Circuit elements U2A 1101, U2B 1103, R4 1105, R5 1107, R6 1109, R7 1111, and D1 1113 all comprise a full wave rectifier circuit for the AC-coupled version of the photodiode signal. Due to the pulsed nature of the LED radiance, the full wave rectifier output should closely resemble a DC voltage level. This voltage level is then fed through R8 1001 (as shown in FIG. 10) to create a signal current into integrator circuit 1000 as shown in FIG. 10. Voltage reference circuit elements U4B 1002, R11 1003, and C4 1005 act to buffer and low-pass filter (through R11 1003 and C4 1005) a −5 volt reference voltage 1201 (as shown in FIG. 12) from the receiver circuit board. The output of op-amp U4B 1002 is fed through R9 1009 to create a reference current into the integrator circuit.

U3B 1011, C3 1013, R21 1015, and Q1 1017 comprise the integrator circuit. The current difference through R8 1001 and R9 1009 is fed to the summing junction of op-amp U3B 1011. This current difference is integrated by C3 1013. U3B 1011 adjusts the base current of Q1 1017 (through R21 1015) according to the rate of change of current into the summing junction.

FIG. 13 shows an electrical schematic of a clock and LED driver 1300. A timer circuit is used to generate the chopper (or pulse) rate for the LED. This circuit is comprised of U5 1309, R14 1301, R15 1303, C5 1305 and C6 1307. A pulse rate of approximately 470 Hz with a duty cycle of approximately 33% is obtained with the chosen components. (Variations of the embodiment may utilize a different pulse rate in order compensate for operating conditions.) U6 1311 is an RS-422 transceiver that is used to transmit the clock differentially to the receiver board as a means to minimize noise coupling into the very sensitive receiver circuitry. Op-amp U4A 1313, in conjunction with R12 1315, R13 1317, and C28 1319 serves as a low current +5V power supply for the clock circuitry.

Q2 1321, R10 1323, R16 1325, R21 1015 (as shown in FIG. 10), C25 1019, C26 1021, and C27 1327 comprise the LED driver circuit (of which transistor Q2 1321 is the centerpiece). The emitter voltage of Q1 1017 is appropriately set by the integrator to drive an LED 1329 through R10 1323 and Q2 1321. The clock circuit provides the pulsed base current (through R16 1325) for Q2 1321, which pulses LED 1329 at the chopper rate. Capacitor C27 1327 is a tailor capacitor that low-pass filters the base current to provide a modified LED current drive. Inclusion of capacitor 1327 significantly reduces both conducted and radiated noise throughout the entire electronics subsystem. R10 1323 is used to monitor the LED current through test points. R21 1015 is needed to maintain emitter current flow through Q1 1017 during the off phases of the clock. C25 1019 and C26 1021 act to smooth the emitter current of Q1 1017 between both phases of the clock. The pulsed LED current was adjusted to approximately 30 mA to provide a high level of LED radiance yet still be within recommended operating parameters. The standard steady-state LED current is 20 mA. The equivalent steady-state current for a 30 mA pulsed current drive at a duty cycle of 33% is 10 mA.

Figure 14:
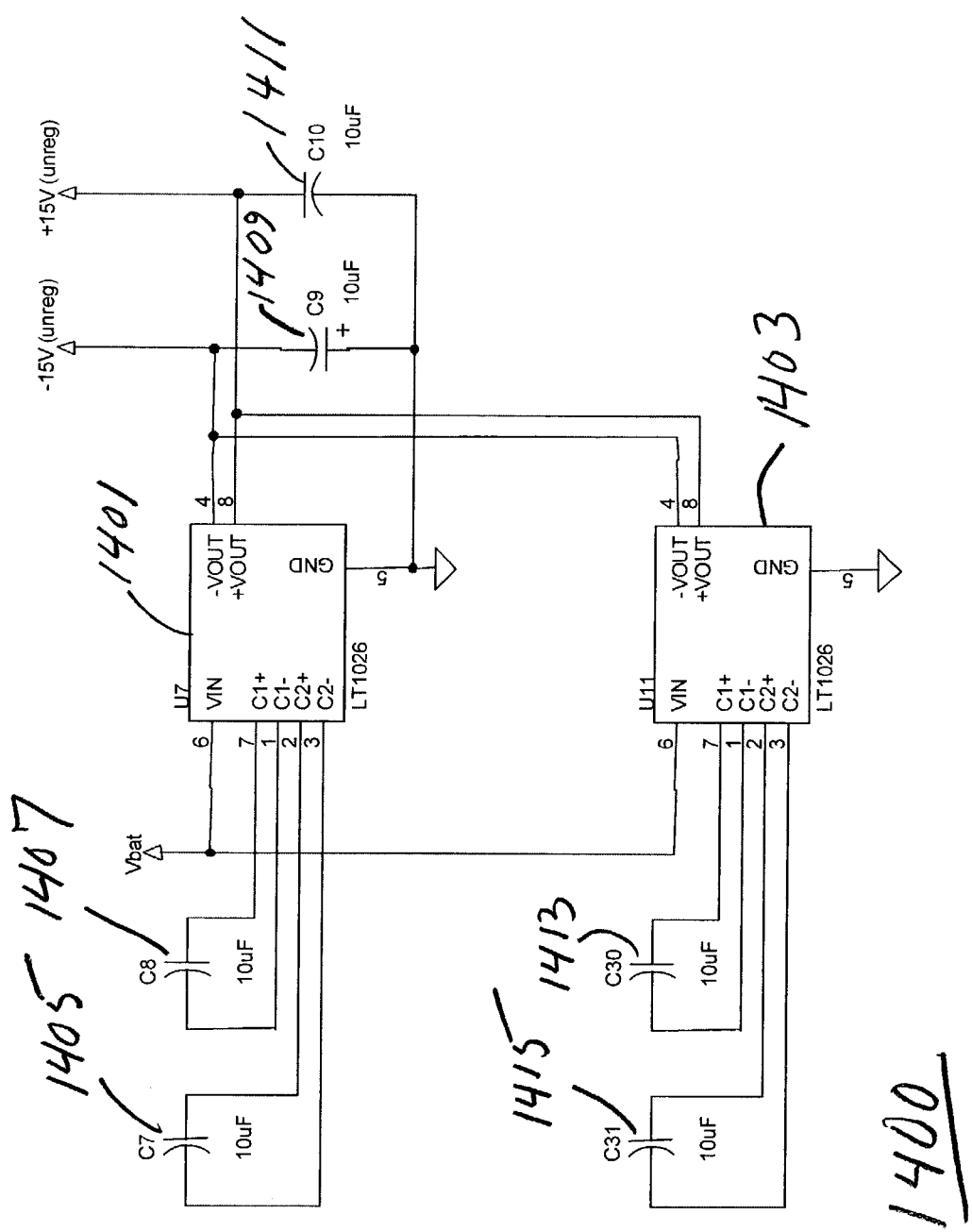
FIG. 14 shows a charge pump switching regulator circuit in accordance with an embodiment of the invention.

A power supply circuit is incorporated to produce multiple, regulated voltage outputs from a single, unregulated battery voltage. FIG. 14 shows a charge pump switching regulator circuit 1400. A miniature charge-pump DC/DC converter circuit (with dual linear post-regulators) is utilized to produce the dual, regulated voltage outputs needed for the instrument's electronics. The regulators' outputs have very low ripple (~1–5 mV RMS).

Eight silver oxide battery cells (not shown) are packaged into an AAA battery holder to provide the required power source for the electronics. A 100 microfarad capacitor is connected across the battery to support the initial current surge of the electronics. The battery holder and capacitor are both mounted directly to the LED driver circuit board. In-situ testing has shown a battery life of approximately 40 minutes when connected to the electronics (which significantly exceeds specification). Output voltage of the battery/capacitor combination under load is approximately 8 volts.

U7 1401 and U11 1403, in conjunction with capacitors C7 1405, C8 1407, C9 1409, C10 1411, C30 1413, and C31 1415 provide a concatenated charge pump for the electronics. This circuit provides both a voltage doubler and inverter for the input battery voltage. C8 1407 and C30 1413 provide the "bucket" capacitors for the positive doubled output voltage, while C7 1405 and C31 1415 are the capacitors for the negative inverted output voltage. C9 1409 is the output current drive capacitor for the negative output voltage, while C10 1411 is used for the positive output voltage. The output voltage values are approximately twice the battery voltage for the positive voltage, and an inverted version of that voltage for the negative voltage. Both of these output voltages are unregulated.

Figure 15:
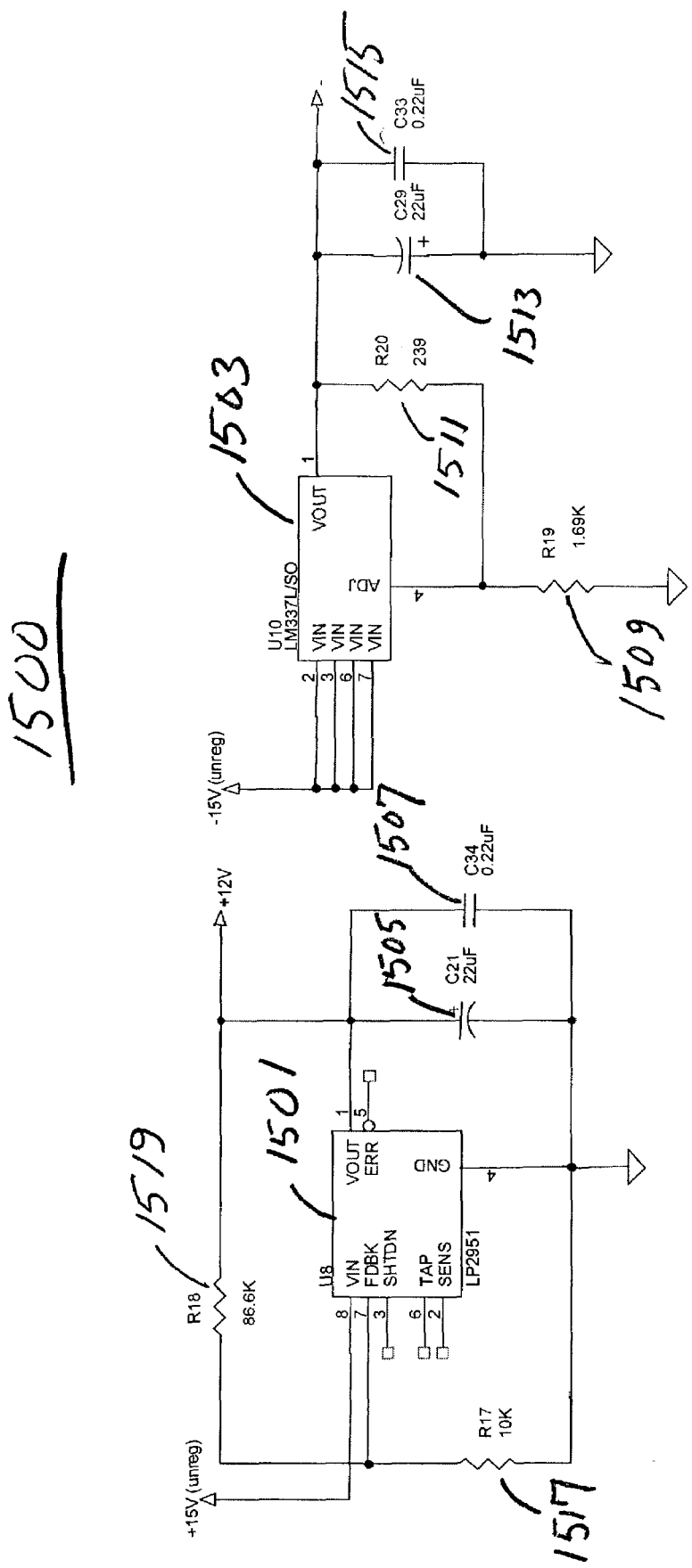
FIG. 15 shows an electrical schematic of the linear post regulators in accordance with an embodiment of the invention.

FIG. 15 shows an electrical schematic of linear post regulators. U8 1501 and U10 1503 are the linear post-regulators for the positive +12V and negative −10V regulated supply rails for the electronics. U8 1501 is a low dropout positive regulator that can maintain regulation to the load down to a dropout voltage across the regulator of 0.5 volts. Resistors R17 1517 and R18 1519 set the regulator output voltage, and capacitors C21 1505 and C34 1507 act to decouple and filter the regulator's output voltage. U10 1503 is a standard negative regulator that can maintain regulation down to a dropout voltage of 2 volts. Resistors R19 1509 and R20 1511 set the output voltage, and capacitors C29 1513 and C33 1515 decouple and filter the output voltage. The output voltage for this regulator (−10V) is set slightly lower than the positive rail (+12V) to allow more voltage overhead to compensate for the 2 volt dropout voltage. Both of these regulators have very low output ripple (approximately 1 to 5 mV RMS).

The second circuit board contains the receiver circuitry. An input photodiode current serves as the input and a frequency modulated pulse train serves as the output. The receiver circuitry contains three functional elements: the transimpedance amplifier, the lock-in amplifier, and the transmitter. Descriptions of these circuit elements are contained in the following sections.

Figure 16:
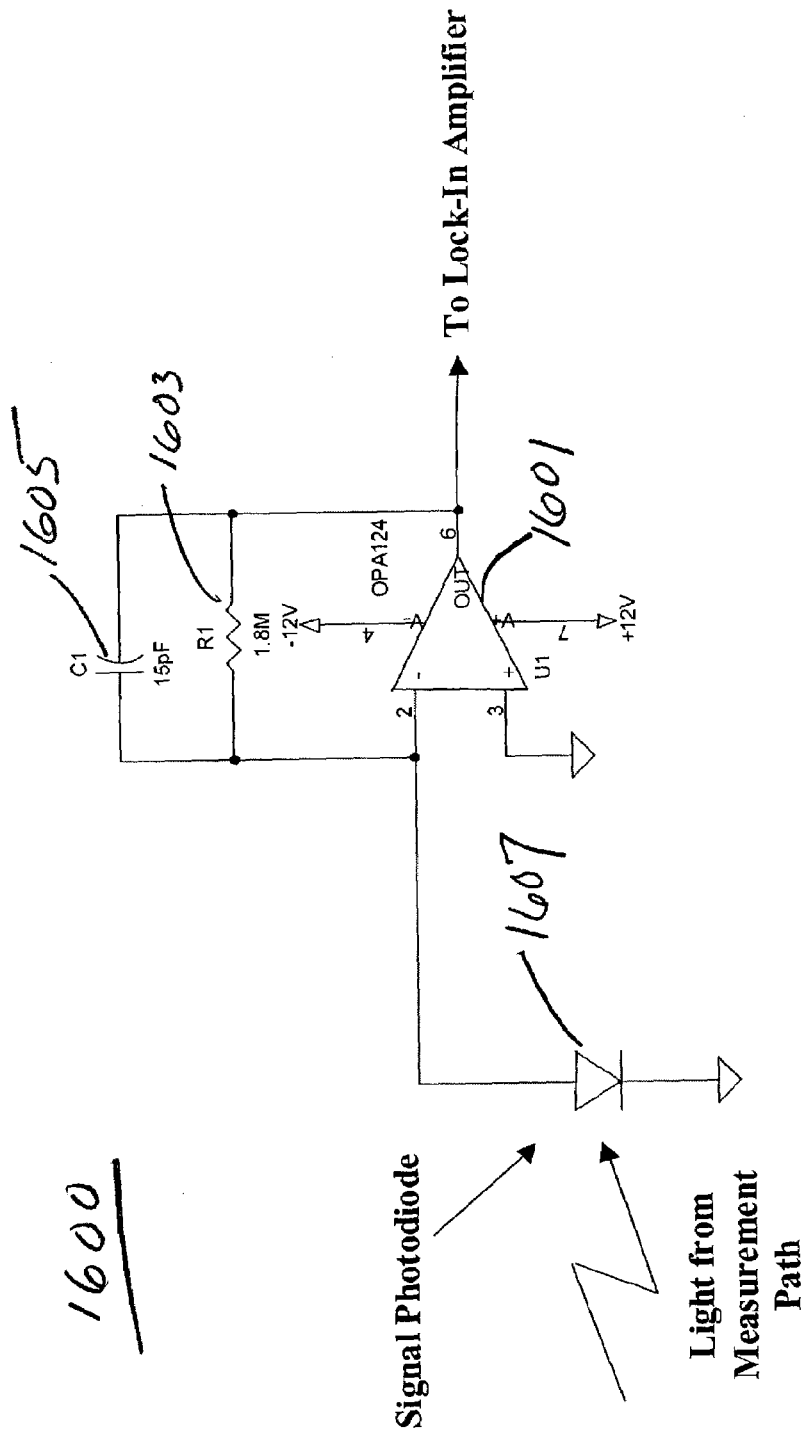
FIG. 16 shows a transimpedance amplifier in accordance with an embodiment of the invention.
Figure 17:
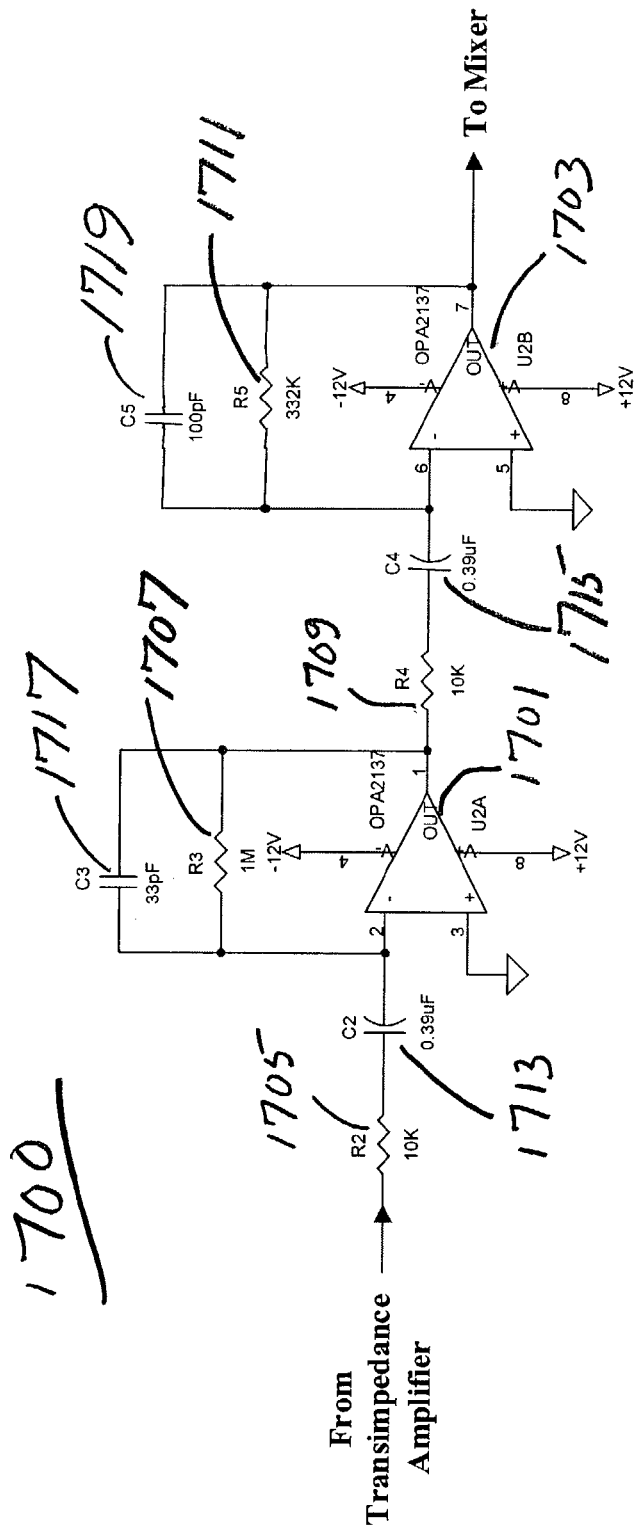
FIG. 17 shows a bandpass filter of the lock-in amplifier in accordance with an embodiment of the invention.

FIG. 16 shows a transimpedance amplifier 1600. U1 1601, R1 1603 and C1 1605 comprise transimpedance amplifier 1600, which converts the receiver photodiode's output current to a low impedance voltage output for further amplification and filtering by bandpass amplifier 1700 (as shown in FIG. 17). R1 1603 sets the gain or transimpedance ($G=R1=V_{out}/I_{in}$) of the circuit, while C1 1605 creates a single pole (combined with R1 1603) in the circuit to prevent significant gain peaking due to the junction capacitance of a photodiode 1607.

A lock-in amplifier's high signal-to-noise performance capability is based on its ability to effectively tune its output in frequency and phase with a known signal clock that is embedded in the input signal. In the embodiment, the signal clock is produced by the actively controlled LED light source. The lock-in amplifier tunes itself to the pulse rate of the LED. The lock-in amplifier includes three functional elements: a bandpass amplifier (see FIG. 17), a mixer (see FIG. 18), and a low-pass filter (see FIG. 19).

FIG. 17 shows a bandpass filter 1700 of lock-in amplifier 415. Op-amps U2A 1701 and U2B 1703 are the active elements of a two-stage bandpass amplifier. The gain of the first stage is G1=R3/R2=100 (corresponding to resistors 1705 and 1707) and the gain of the second stage is G2=R5/R4=33 (corresponding to resistors 1709 and 1711), making the total gain=G1*G2=3300. The high pass filter elements are R2 1705 and C2 1713 for the first stage, and R4 1709 and C4 1715 for the second stage. The low pass filter elements are R3 1707 and C3 1717 for the first stage, and R5 1711 and C5 1719 for the second stage. The primary purpose of the bandpass amplifier is to amplify the pulsed signal from transimpedance amplifier 1600 while filtering out of band low frequency noise from DC sunlight and surface wave focused light and broadband Johnson/shot noise from electronics and the same DC/surface wave focused light.

Figure 18:
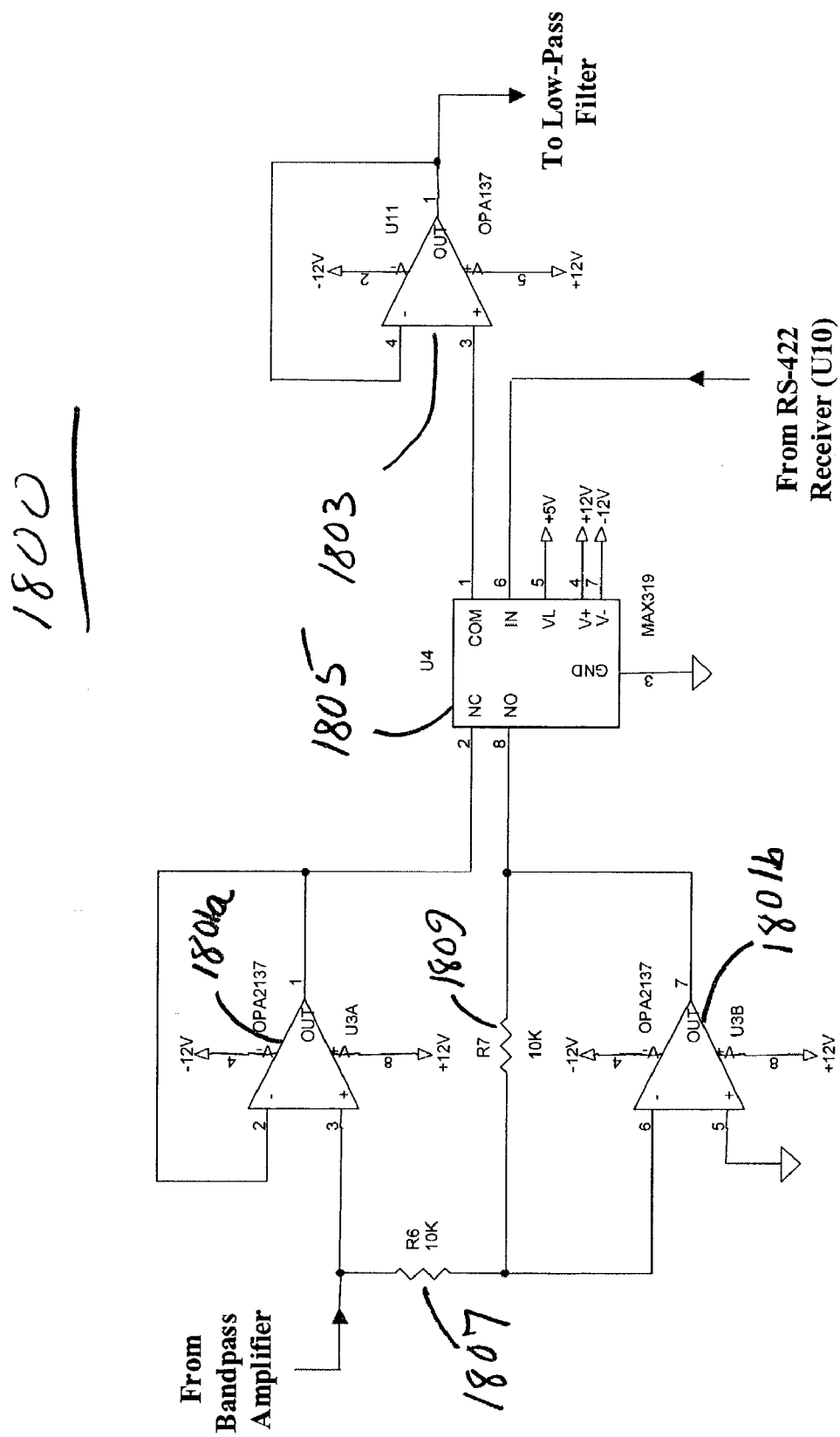
FIG. 18 shows a mixer element for the lock-in amplifier in accordance with an embodiment of the invention.

FIG. 18 shows a mixer element 1800 for lock-in amplifier 415. Mixer 1800 comprises op-amps U3 1801a and 1801b, U11 1803, SPDT switch U4 1805, and resistors R6 1807, R7 1809. The mixer acts to sample the input waveform on alternating phases of the LED clock, thus acting to demodulate and lock-in the input waveform. U3A 1801a is configured as a voltage follower to produce the non-inverted switch input, and U3B 1801b is configured as an inverter (with R6 1807 and R7 1809) to produce the inverted switch input. Switch 1805 is the centerpiece of mixer 1800, and U11 1803 is configured as a follower to electrically decouple the switch from the low-pass filter stage.

Figure 19:
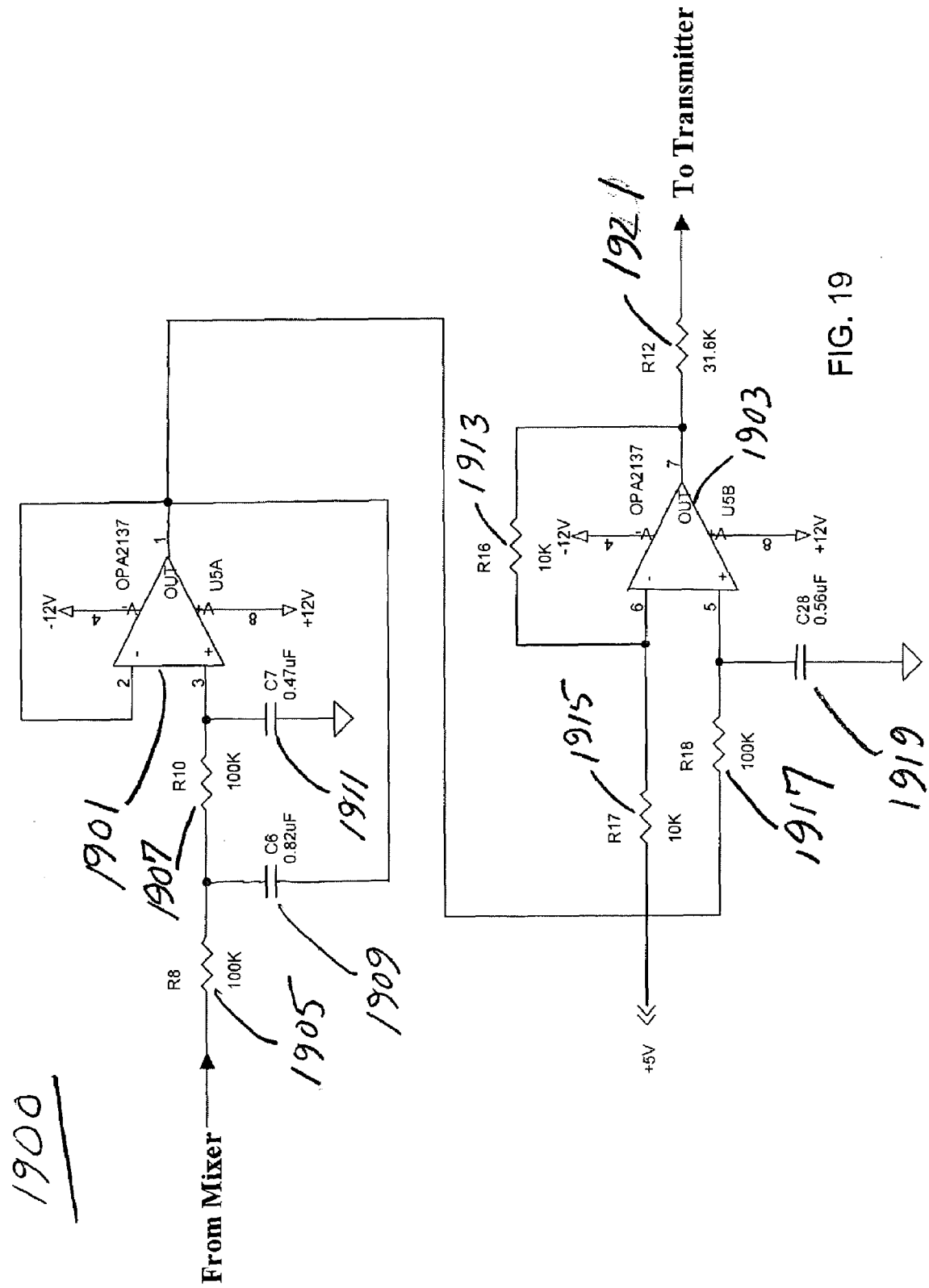
FIG. 19 shows a low pass filter for the lock-in amplifier in accordance with an embodiment of the invention.

FIG. 19 shows a low pass filter 1900 for the lock-in amplifier 415. Low pass filter 1900 functions to complete the demodulation process and convert the locked-signal from mixer 1800 to a baseband signal. Op-amps U5A 1901 and U5B 1903 are the active elements of a two-stage 3-pole low pass filter with DC offset. The first stage includes U5A 1901, R8 1905, R10 1907, C6 1909, and C7 1911. It is a 2-pole low pass filter. The second stage includes U5B 1903, R16 1913, R17 1915, R18 1917, and C28 1919. It is a single pole low pass filter with a DC offset. The DC offset is produced from a +5V reference voltage through gain resistors R16 1913 and R17 1915. This forced DC offset is necessary to stabilize the voltage to frequency converter circuit as will be discussed.

Figure 20:
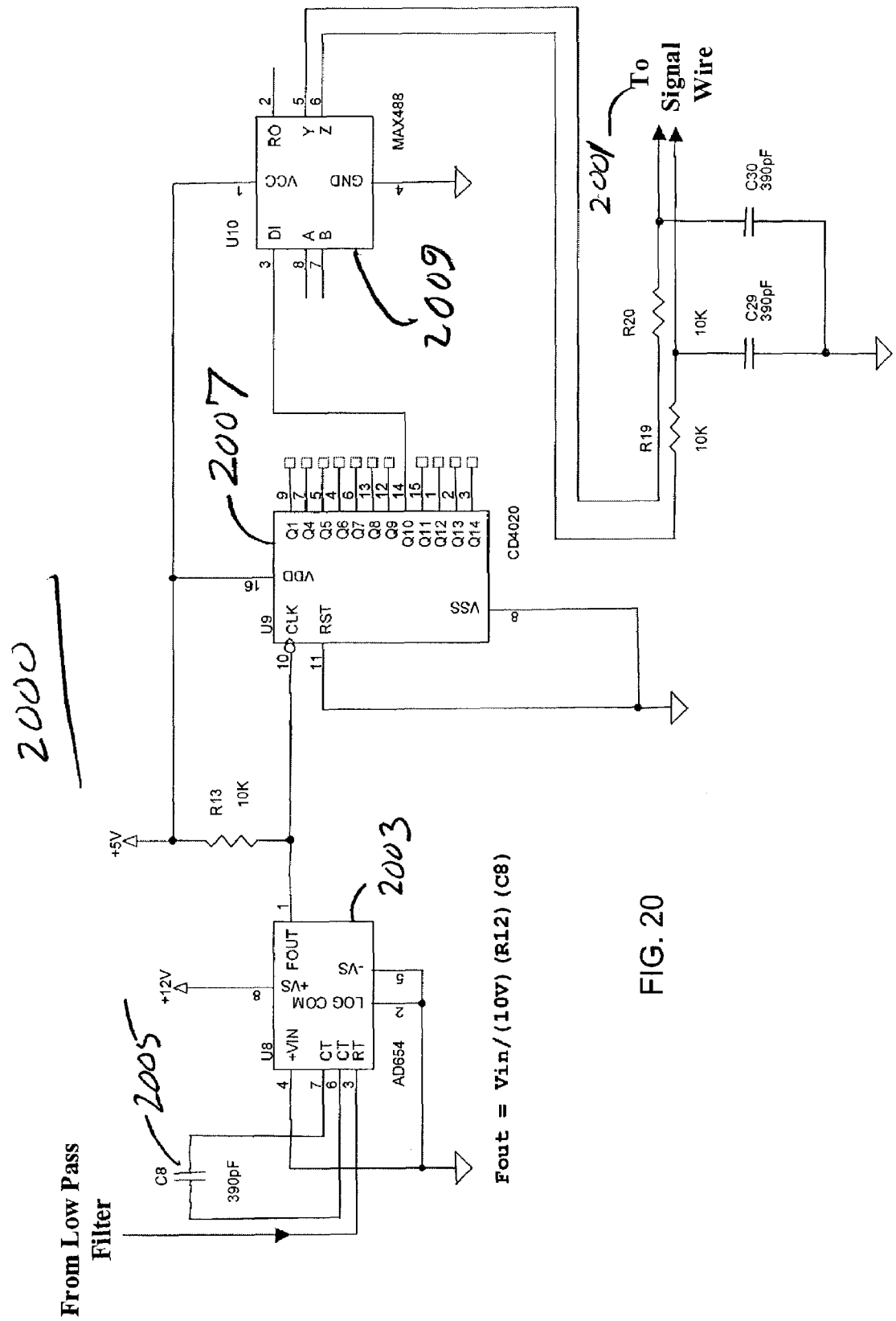
FIG. 20 shows a transmitter circuit for sending information to a calculating unit in accordance with an embodiment of the invention.

FIG. 20 shows a transmitter circuit 2000 for sending information to a calculating unit (not shown). Transmitter 2000 converts the very low frequency DC signal output from low pass filter 1900 to a differential, frequency modulated, digital signal for transmission over a signal wire 2001 to the calculating unit. U8 2003 is a voltage to frequency (V/F) converter that, in conjunction with R12 1921 (shown in FIG. 19) and C8 2005, is configured to produce a 70 kHz pulse train (approx.) as a maximum signal frequency under clear water conditions. The V/F output is then fed into a binary counter 2007 configured as a 10-bit counter (divide by 1024). This reduced frequency output is finally fed into an RS-422 driver 2009 for final output to signal wire 2001. The reduced frequency signal is needed to successfully complete the long journey (approximately 9000 feet) over signal wire 2001 to the calculating unit, where an RS-422 receiver (not shown) is located.

Mechanical Subsystem Design

The primary function of the mechanical subsystem design is to provide a watertight pressure vessel and mechanical support for the electro-optics subsystems. The mechanical subsystem is also designed to provide the required hydrodynamic forces for a proper descent rate and attitude from the surface. As previously mentioned, the mechanical subsystem design consists of three parts: the electro-optics housing, the combination nose/retroreflector housing, and the housing support frame. The embodiment provides an environmental probe that allows full testing of the optics and electronics but retains a high degree of manufacturing for later revisions (i.e. production designs).

Figure 21:
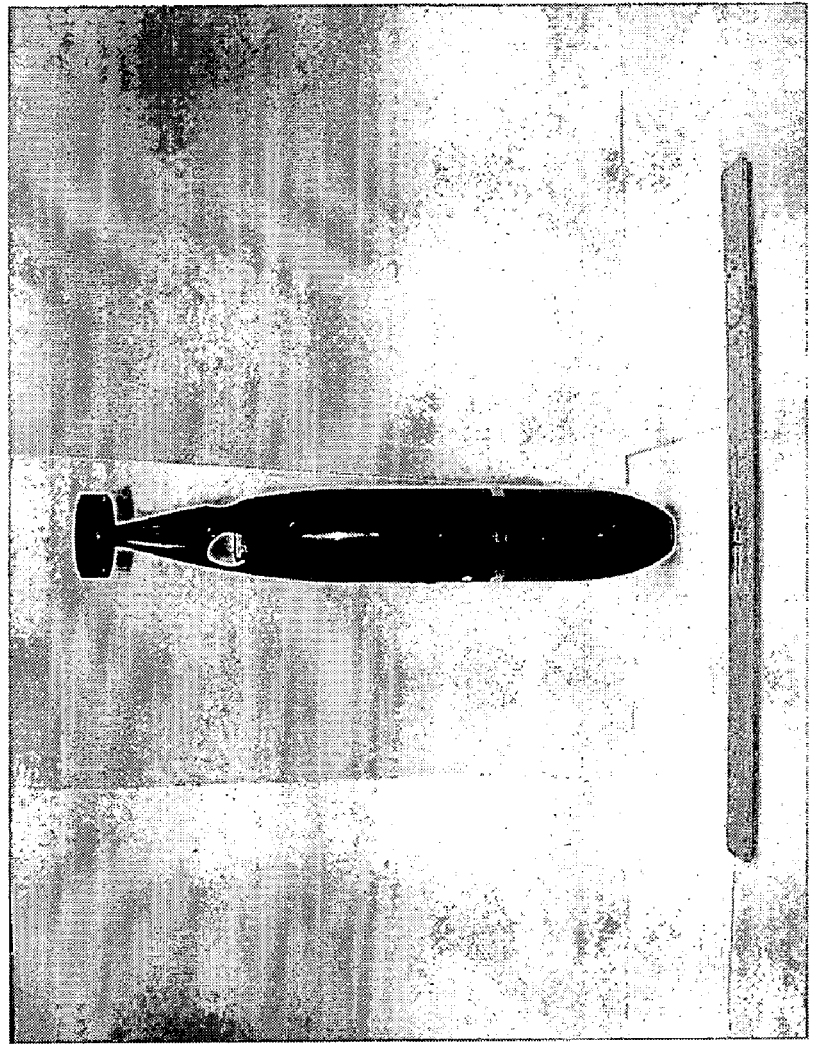
FIG. 21 shows a probe that carries the beam transmissometer in accordance with an embodiment of the invention.
Figure 22:
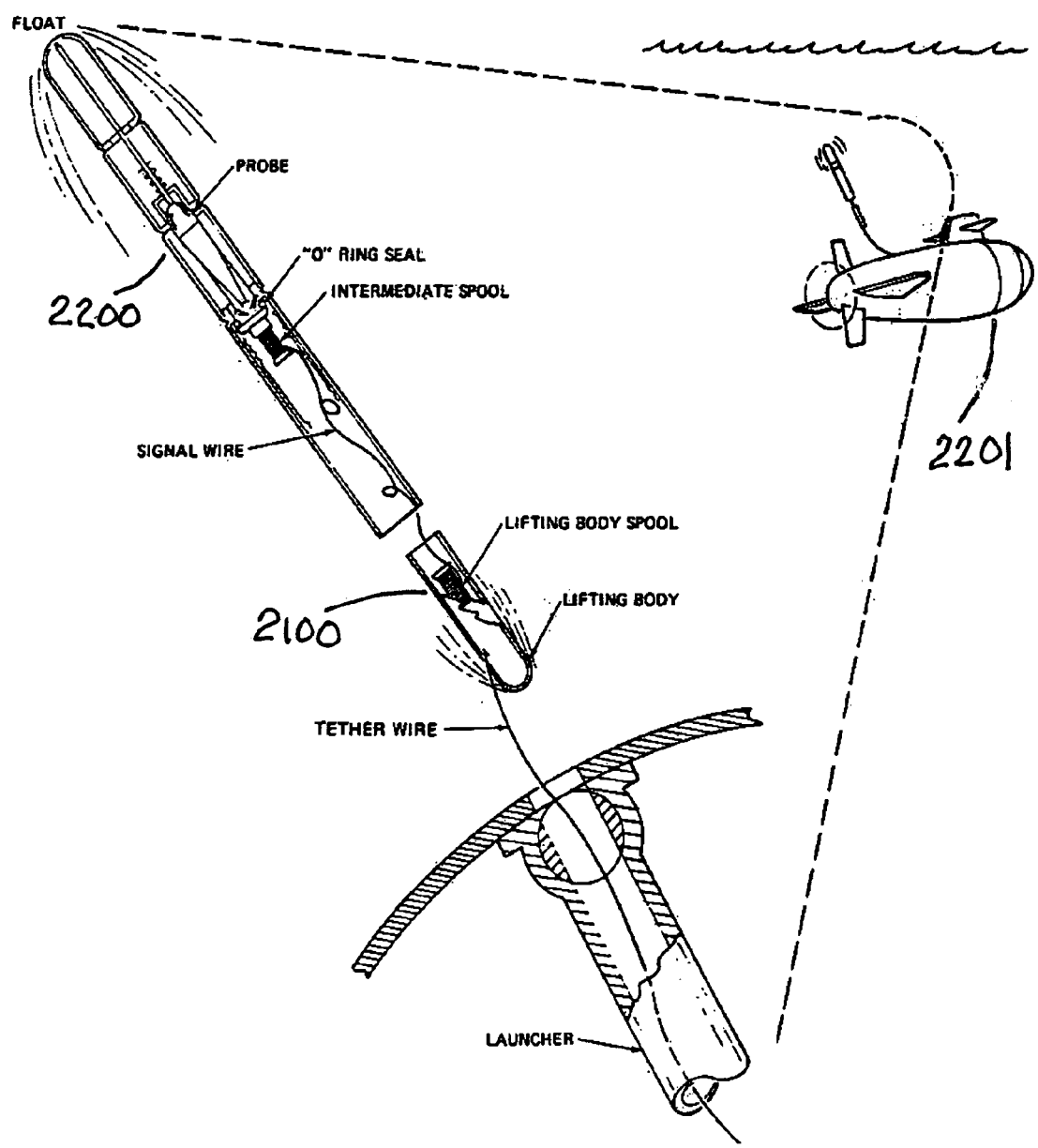
FIG. 22 shows a probe deployment in which the float assembly separates in accordance with an embodiment of the invention.
Figure 23:
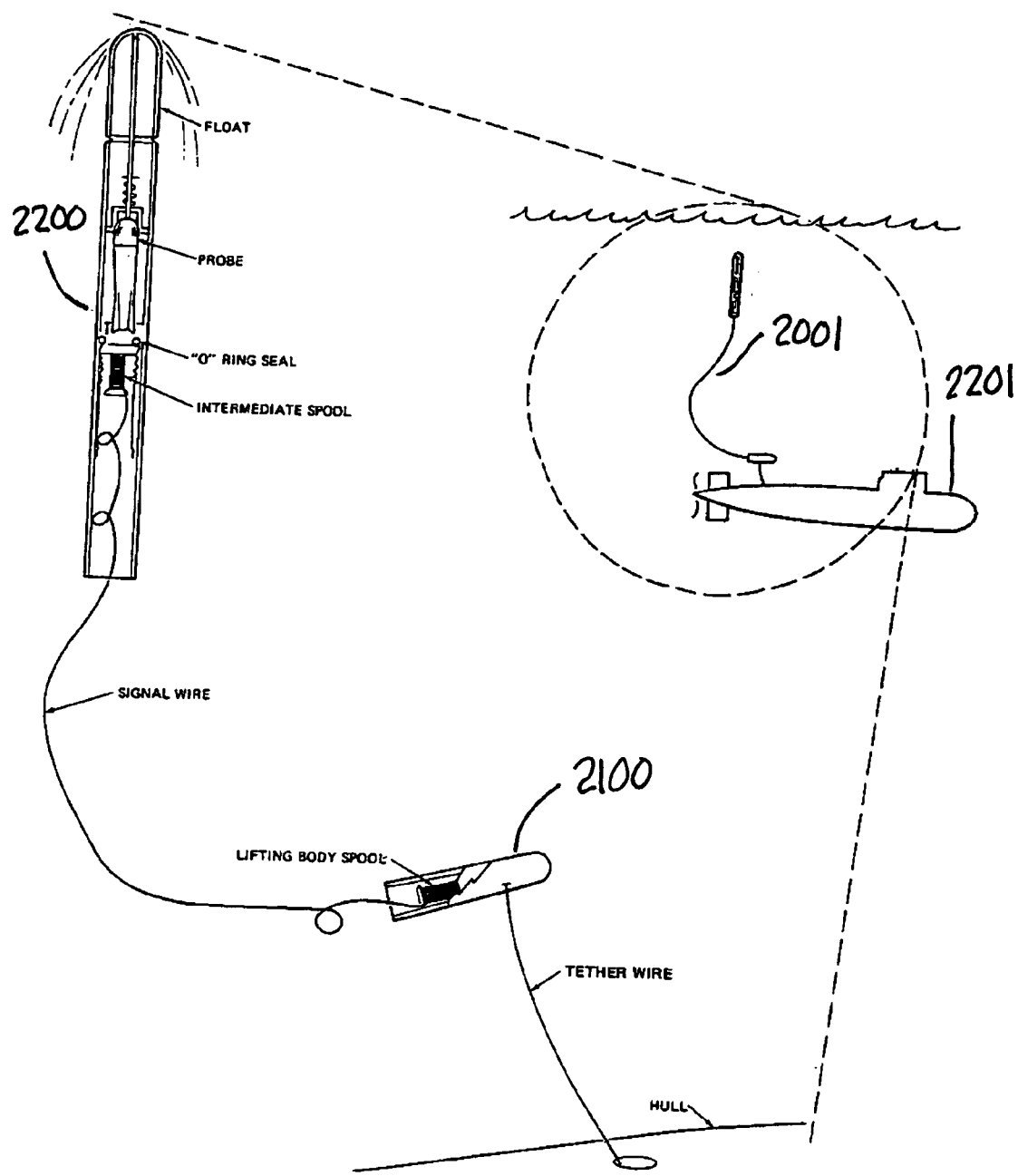
FIG. 23 shows a probe deployment in which the float assembly ascends in accordance with an embodiment of the invention.
Figure 24:
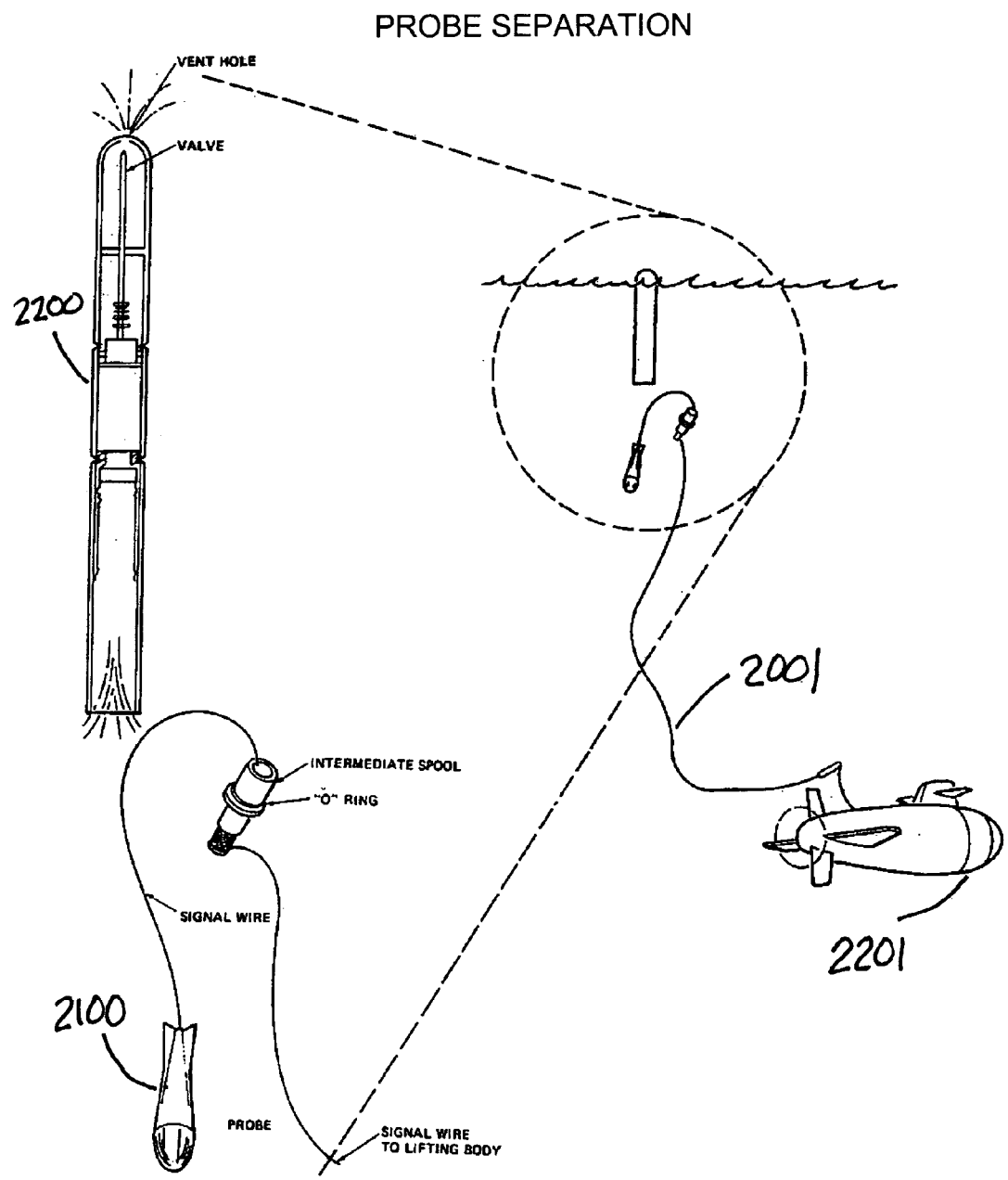
FIG. 24 shows a probe deployment in which the probe separates in accordance with an embodiment of the invention.
Figure 25:
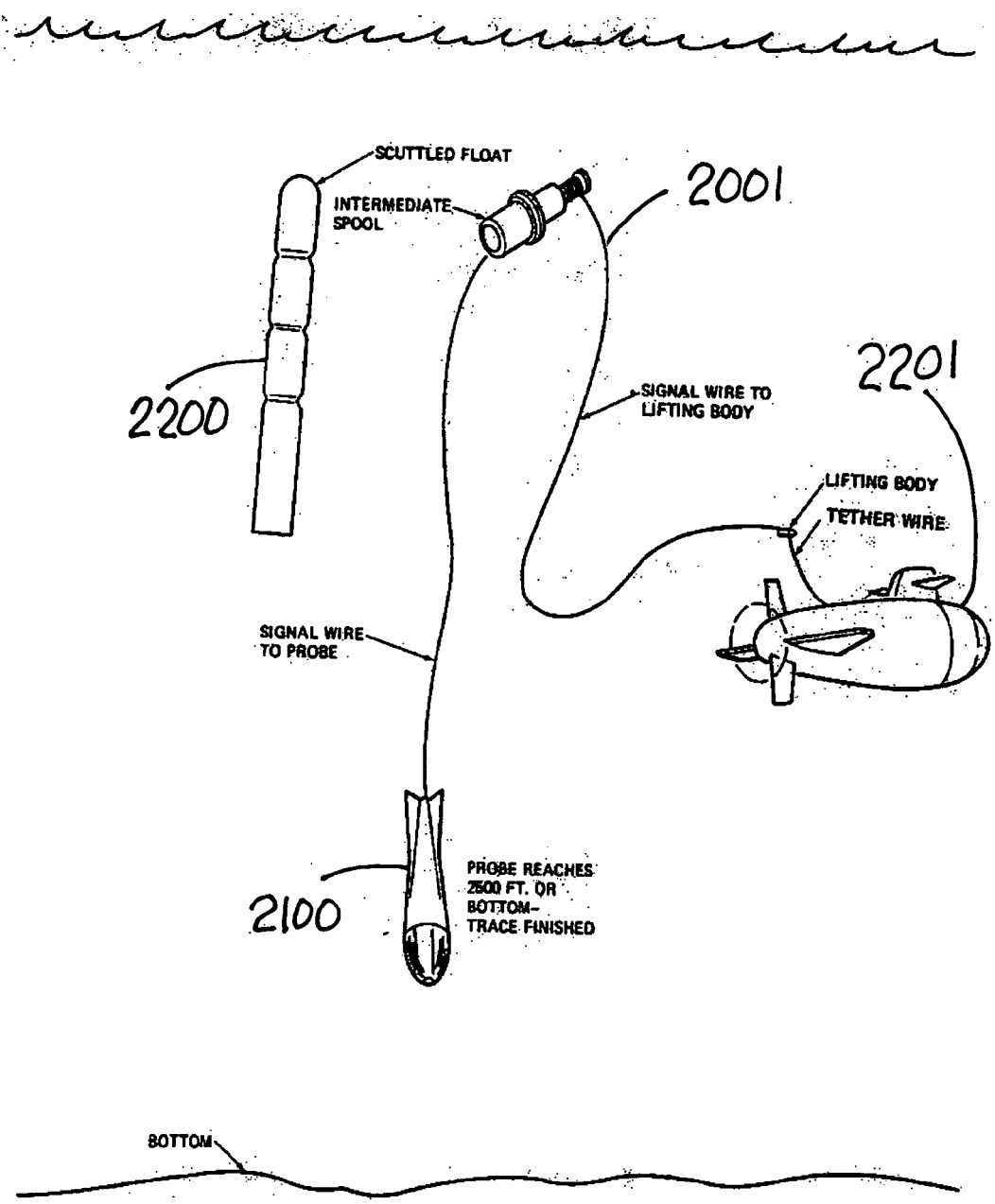
FIG. 25 shows a probe deployment in which the launch completes in accordance with an embodiment of the invention.

FIG. 21 shows a probe 2100 that carries the beam transmissometer in accordance with an embodiment of the invention. Probe 2100 is deployed in casting 2200 as shown in FIG. 22. FIGS. 22, 23, 24, and 25 show a deployment of probe 2100 at different phases of a launch. Probe 2100 is released when casing 2200 reaches the surface (as shown in FIG. 22. The depth of probe 2100 during the descent is not transduced from a pressure sensor, but instead determined from the drop rate of probe 2100 which is established through design, empirical testing and modeling. For that reason, particular attention should be paid to the center of gravity, center of buoyancy, metacentric height, total weight (in water), buoyancy, drag and any other parameters affecting the overall dynamics of probe 2100 as it travels through the water. In the embodiment, probe 2100 comes with a tri-vaned cylindrical tail section that causes the probe to rotate as it descends at a rate of 10–16 rev/sec. This enhances the vertical stability of probe 2100 and also serves to destabilize the boundary layer as probe 2100 spins. Probe 2100 may actually slow down as probe 2100 descends due to the increased buoyancy as signal wire 2100 is expended.

Figure 26:
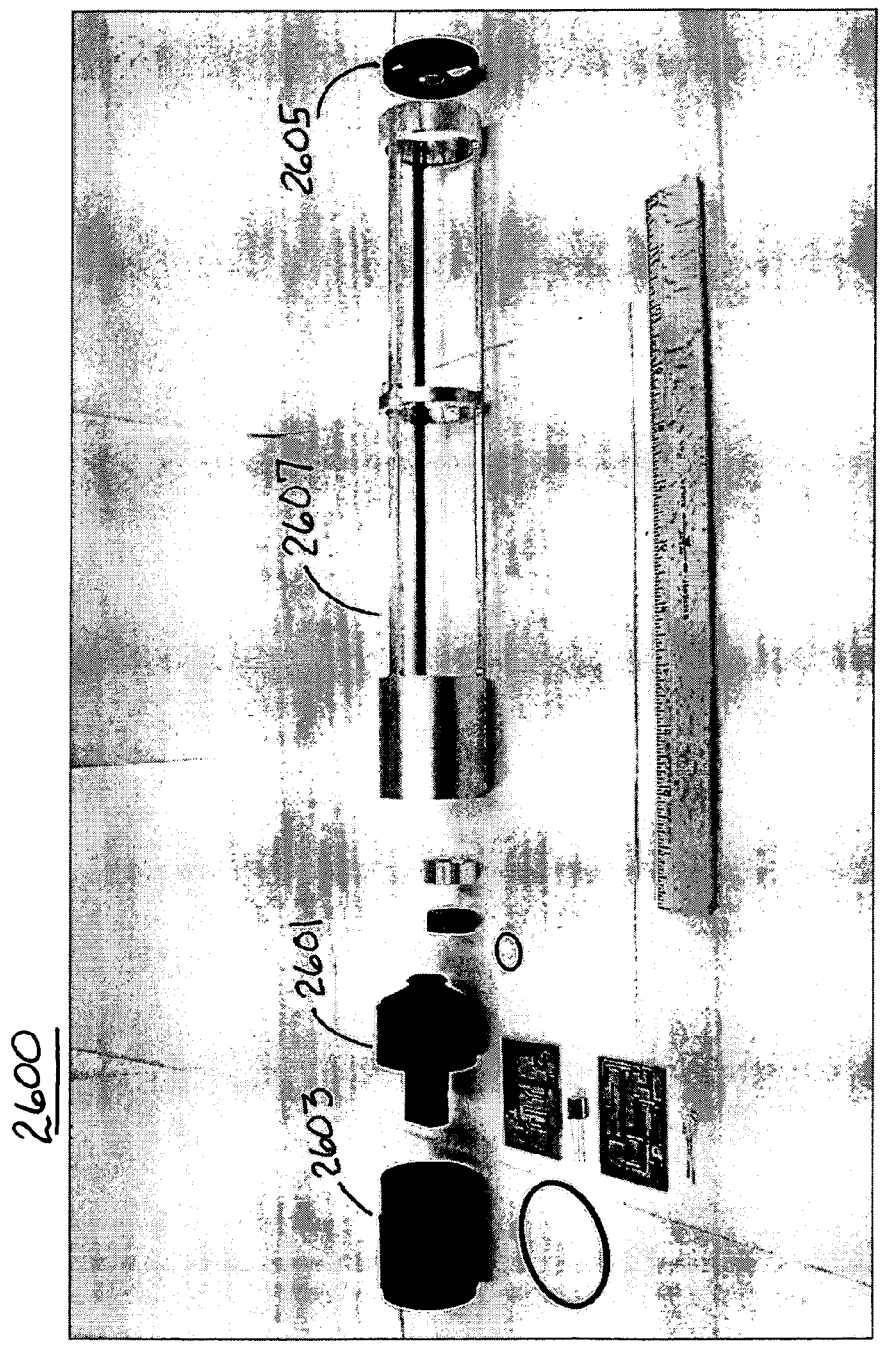
FIG. 26 shows an expanded view of an expendable transmissometer in accordance with an embodiment of the invention.
Figure 27:
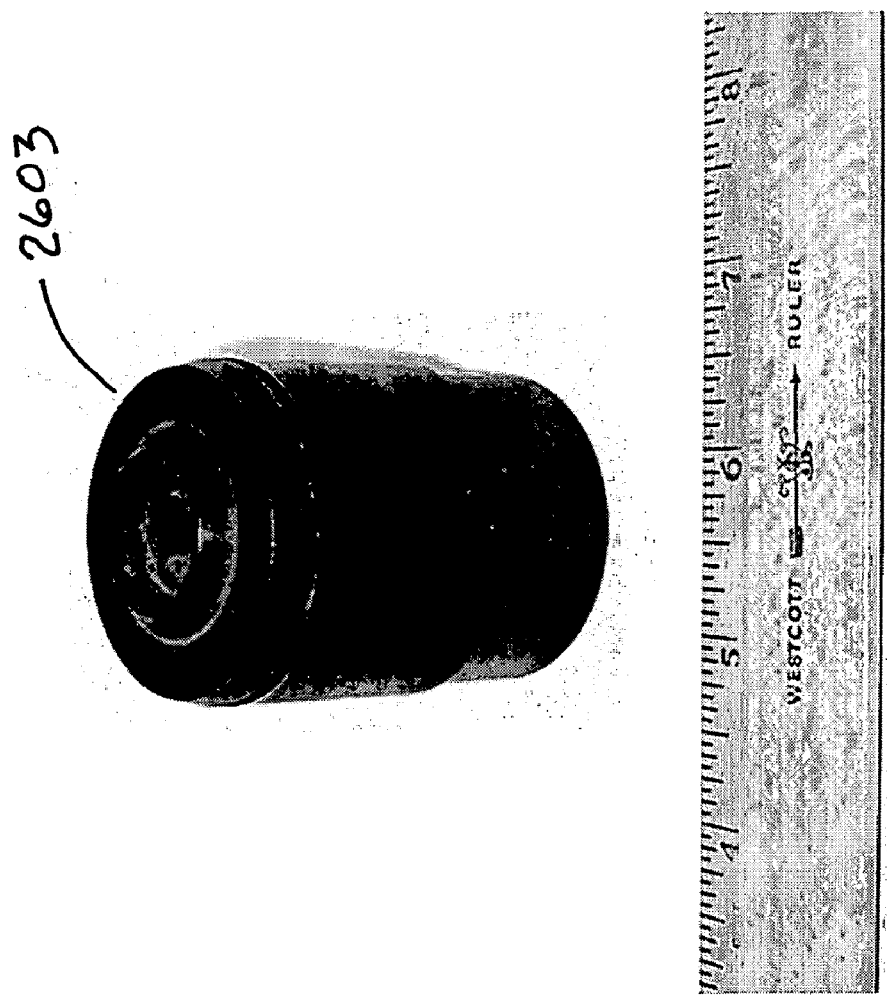
FIG. 27 shows a pressure proof cap of an electro-optics housing in accordance with an embodiment of the invention.
Figure 28:
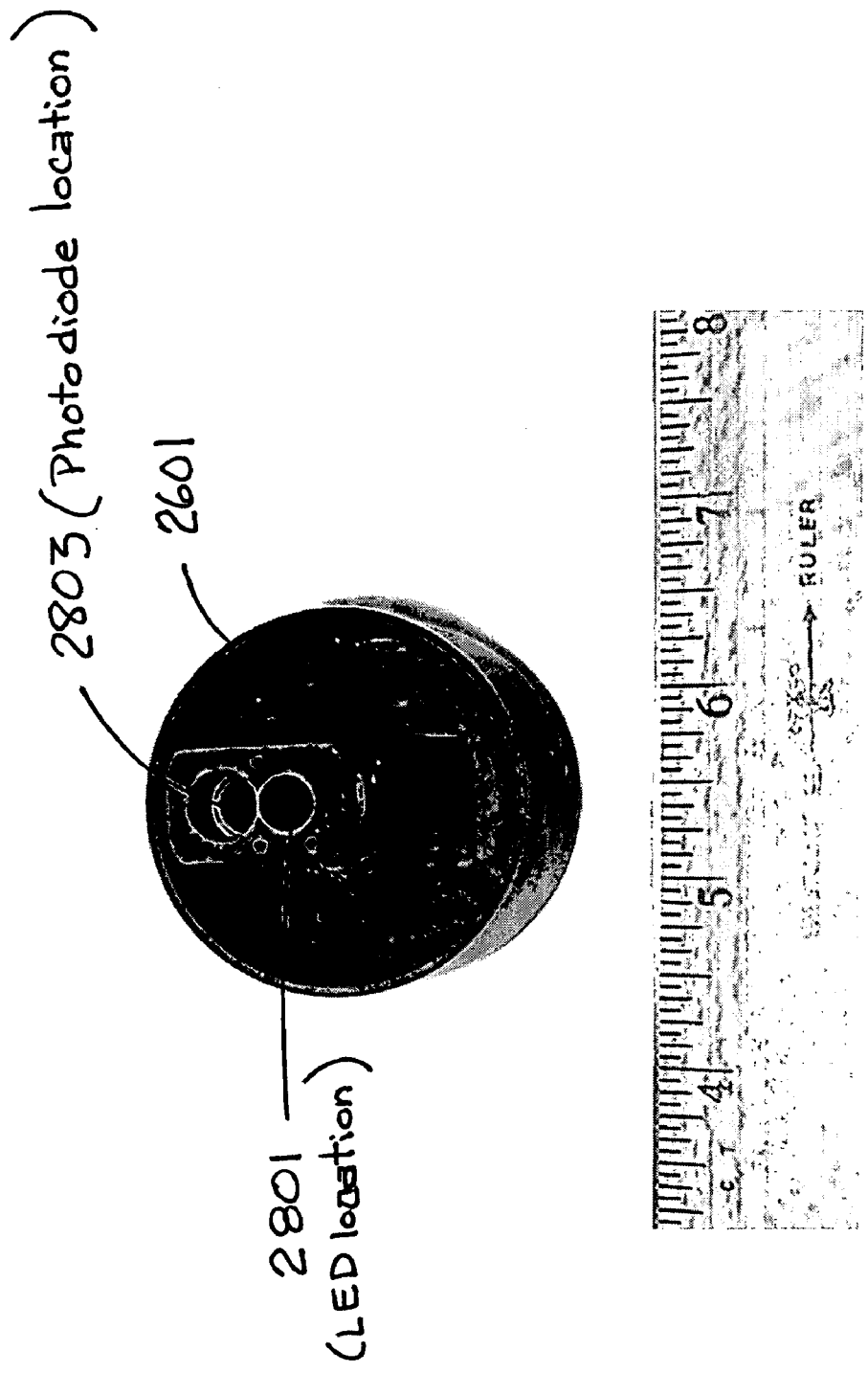
FIG. 28 shows a transmitter and receiver in the electro-optics housing in accordance with an embodiment of the invention.
Figure 29:
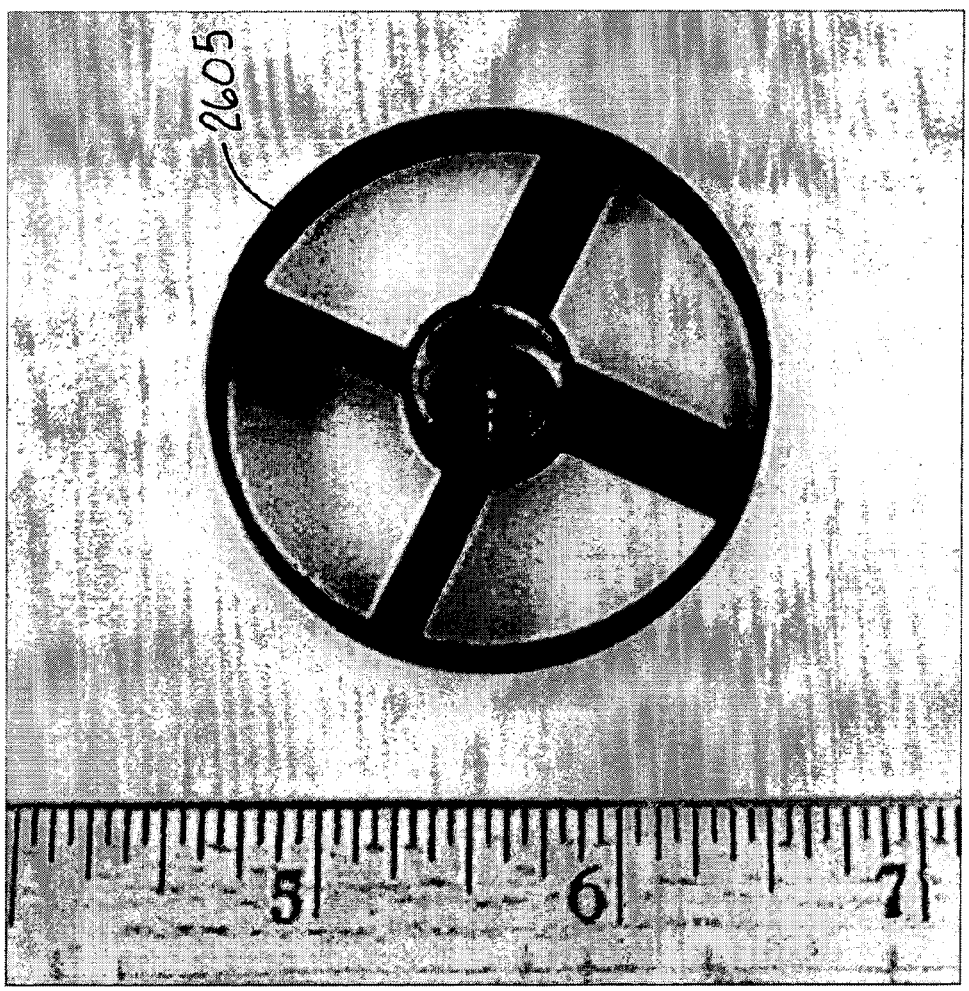
FIG. 29 shows a nose/retroreflector housing in accordance with an embodiment of the invention.
Figure 30:
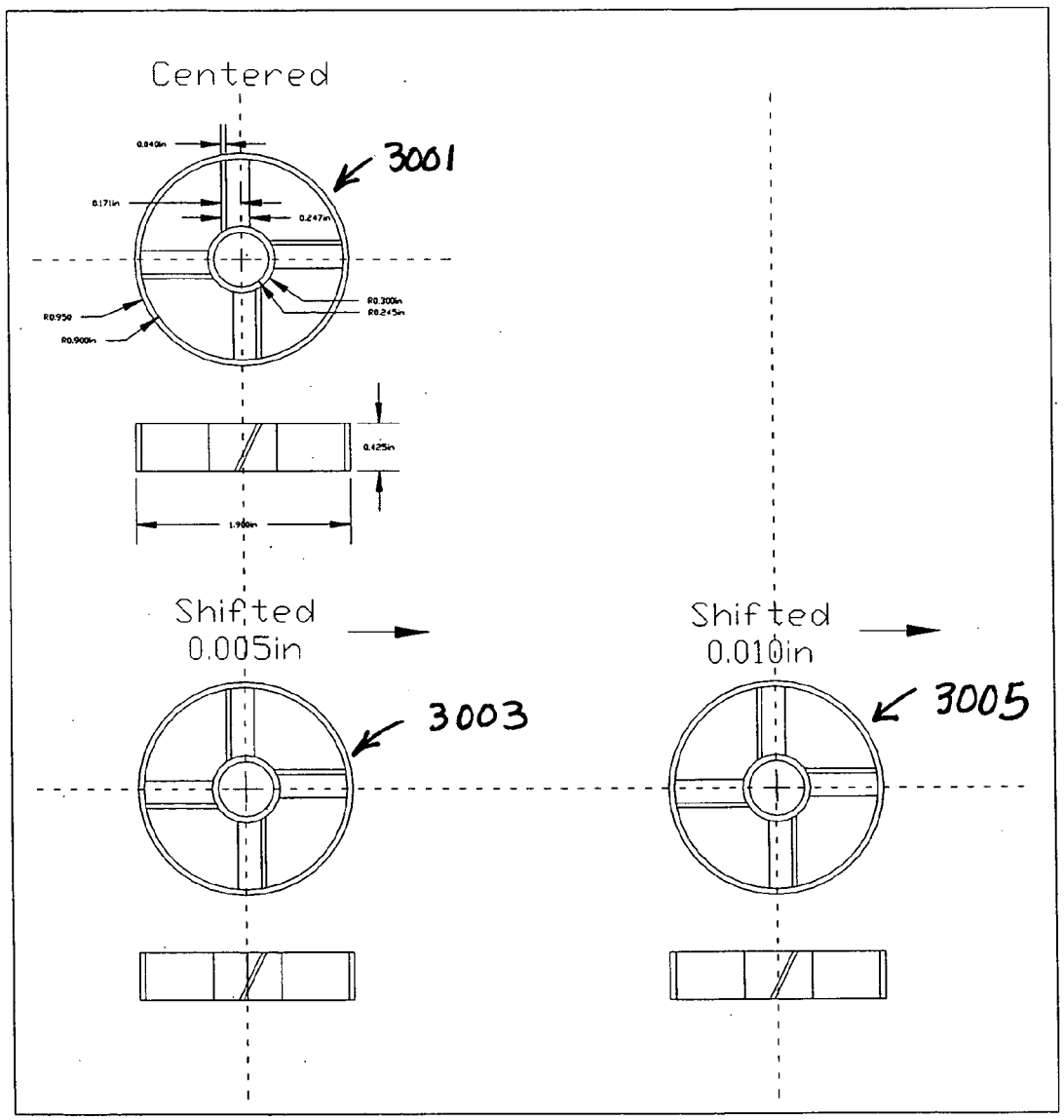
FIG. 30 shows details of the retroreflector housing as shown in FIG. 29 in accordance with an embodiment of the invention.

FIG. 26 shows an expanded view of an expendable transmissometer 2600. The Electro-Optics housing contains several components. The two large outer casing components (2601 and 2603) are fabricated from 2 inch diameter black Acrylonitrile-Butadine-Styrene (ABS) rod. ABS is a rigid thermoplastic that has very high impact strength, excellent high and low temperature performance and it is resistant to many chemicals. Pressure proof cap 2603 provides one part of a watertight enclosure for the entire housing as well as the electrical and mechanical interfaces to the probe tail. The aft end of pressure proof 2603 has several hermetic feedthroughs for the four 0.05" diameter Samtec pins. These holes allow testing of the probe prior to final sealing. The cavity in which these wires pass is sealed with an epoxy, forming a waterproof barrier. The aft end of the component interfaces to the tri-vaned tail section previously mentioned. FIG. 28 shows a transmitter and receiver in electro-optics housing 2601. All of the optical components are inserted into the two circular tubes labeled "LED location" 2801 and "Photodiode location" 2803. The optics train for both the LED and photodiode is lined with aluminum alignment tubes that are coated black to prevent internal reflections. The aluminum tubes also act to position and lock the lens within the housing. The batteries used to power this sensor are also located in this housing. Eight, 1.5V MS76 series silver oxide batteries are used to provide the 12 volts power for driving all the internal electronics. Four batteries are stacked in an assembly and the two assemblies are placed around the circumference of the housing at 180 degrees apart to retain symmetry in weight and balance for the sensor. The front end probe 2100 is designed to provide multiple functionality in support of the optics train and the hydrodynamic performance. This component, called a nose/retroreflector housing 2605, is shown in FIG. 29. Since the retroreflector should be held at some constant, predetermined and fixed location from the transmitter and receiver optics, a suitable position was designed as an integral part of the probe nose. The center of the housing, detailed in FIG. 30, is used to mount the coated glass retroreflector. Epoxy glue is used to lock the retroreflector in place to the black ABS housing. As will be discussed, retroreflector housing 2605 is later adjusted to tune the optical path, as will be explained. Thus, retroreflector housing 2605 provides two optical functions for probe 2100: a fixed, on-axis location for the corner cube, and an adjustable alignment piece for the optics train.

This front end of housing 2605 requires a two-collar assembly comprised of a plastic sealing collar and an aluminum retaining ring. The plastic sealing collar is fitted to the cylindrical mount in the center of the piece. This plastic collar locks the borosilicate window to the housing and provides the clamping force required to seal the single piston O-ring seal on the electro-optics housing. The aluminum retaining ring slides over the plastic collar to ensure the clamping provided by the plastic collar is maintained.

The second function for housing 2605 is related to the hydrodynamics of probe 2100 itself. The nose is designed with multiple (4) canted vanes that model the 3 vanes in the aft tail section of the probe. These vanes are designed to allow flow of water through the optics path as the probe descends, decrease drag and augment the rotation caused by the tail fins. A small bullet shaped piece of lead is placed at the very nose of the housing 2605 in order to emulate the lead nosepiece of other types of probes. The weight acts to create the overturning moment when probe 2100 initially broaches the surface and begins its descent.

Figure 31:
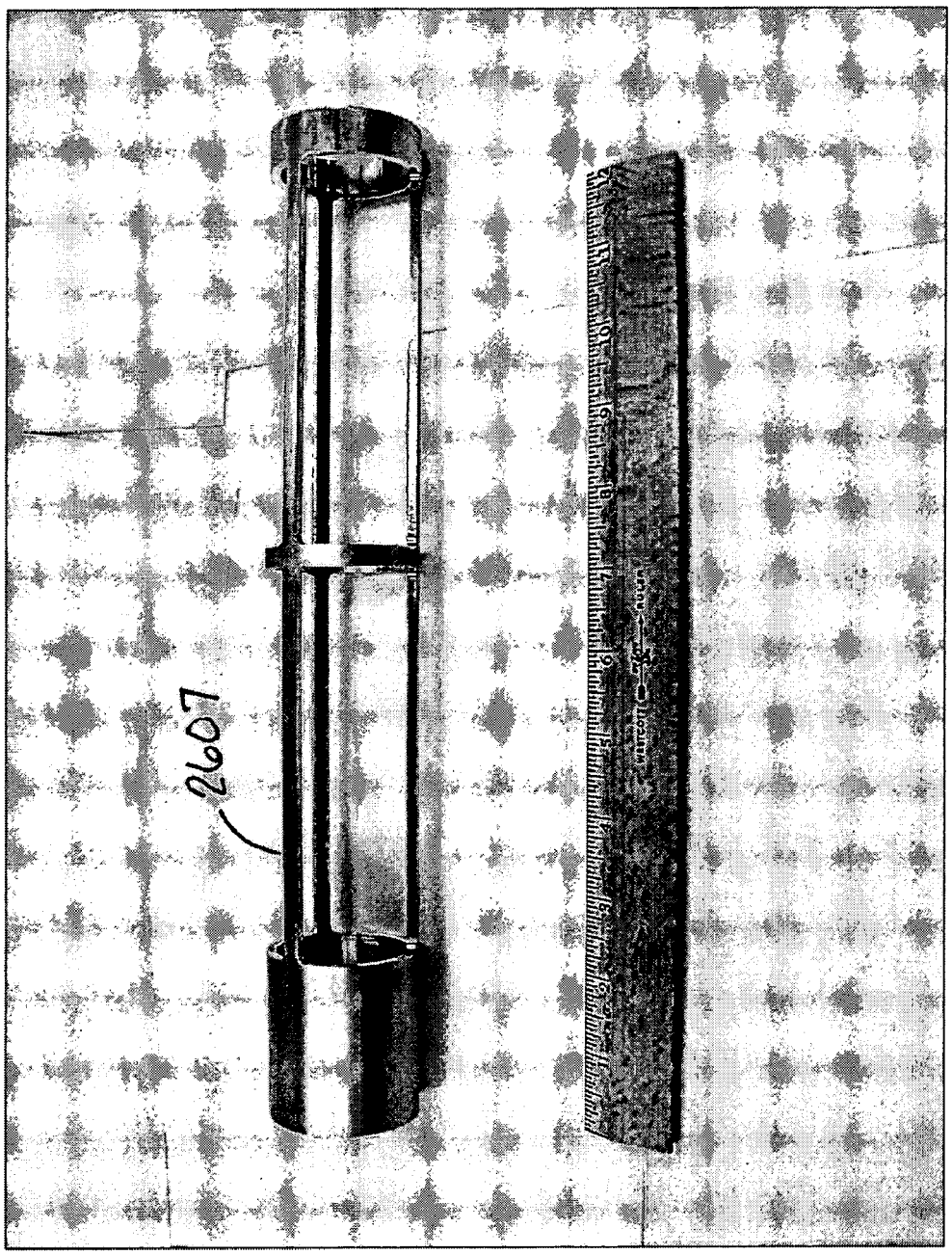
FIG. 31 shows a housing support frame in accordance with an embodiment of the invention.

FIG. 31 shows a housing support frame 2607 (as shown in FIG. 26). Housing support frame 2607 is the mechanical mount for both the nose/retroreflector housing 2605 and the pressure proof cap/electro-optics housing assembly 2603/2601. Support frame 2607, constructed from 2 inch diameter aluminum 6061-T6 tubing. It is designed to allow maximum water flow through the optical path yet provide enough stiffness to the probe to insure the alignment so painstakingly set in the laboratory is maintained during deployment. Both ABS end pieces (the pressure proof cap/electro-optics housing assembly 2603/2601 and nose/retroreflector housing 2605) are attached to the housing support frame 2607 with epoxy glue.

Figure 32:
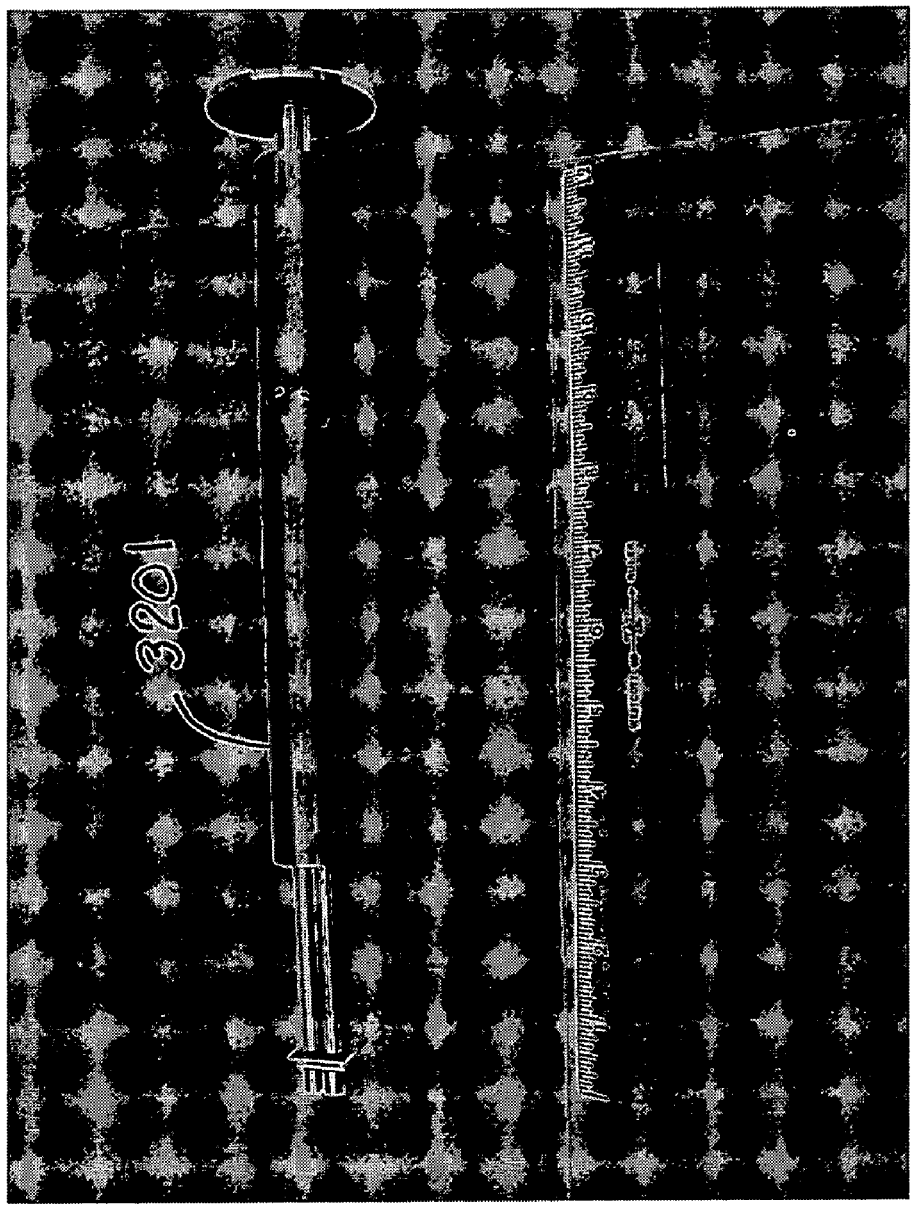
FIG. 32 shows a tool for alignment a transmissometer in accordance with an embodiment of the invention.
Figure 33:
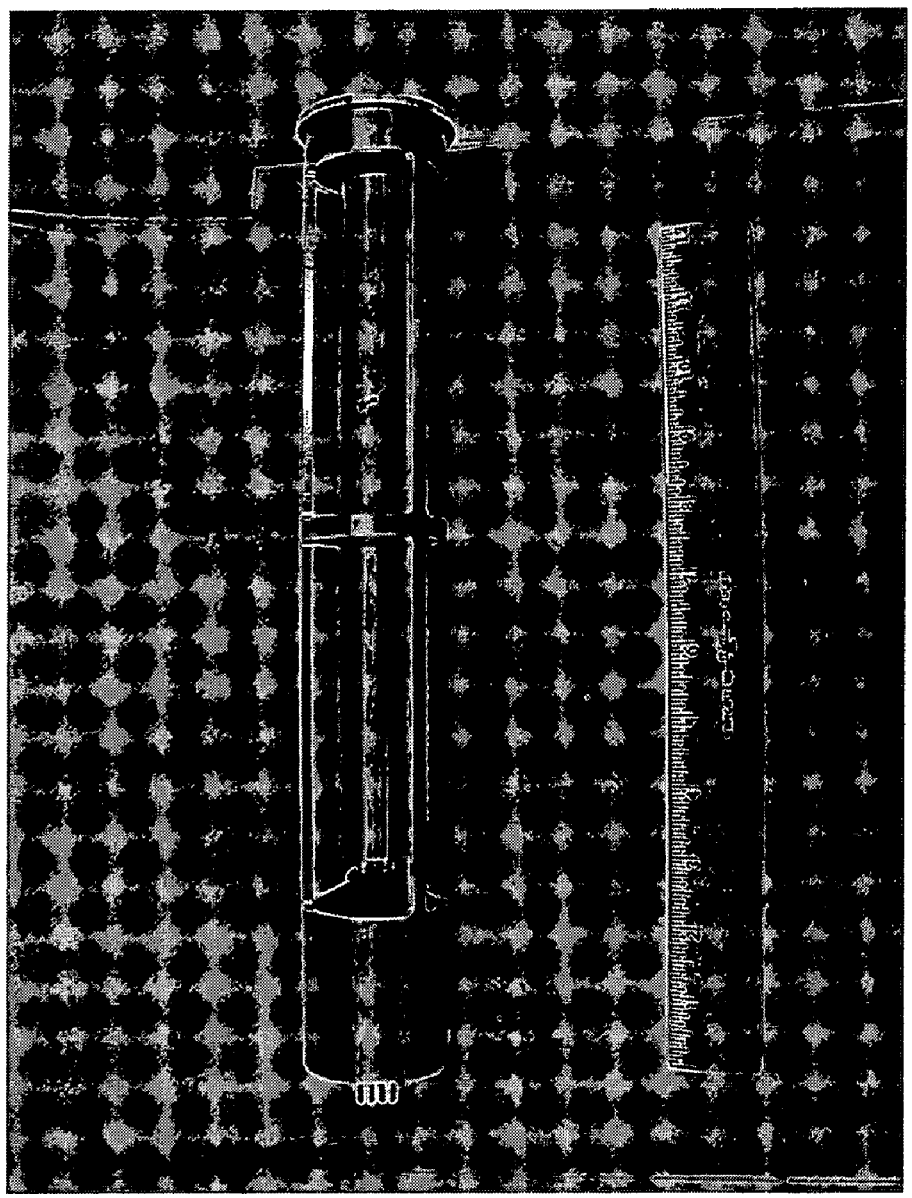
FIG. 33 shows the tool as shown in FIG. 32 attached to a transmissometer in accordance with an embodiment of the invention.

FIG. 32 shows a tool 3200 for alignment beam transmissometer 400. FIG. 33 shows tool 3201 attached to a trans missometer 400. In the embodiment, beam transmissometer may be aligned by the following process:
1. Place the transmissometer on an optics vise to prevent movement.
2. Apply 20 ma of current into the LED.
3. Place a corner cube into a corner cube mount (type 1, corresponding to a corner cube 3001 in FIG. 30). The type 1 mount holds the corner cube along the centerline of the housing support frame. The type 2 mount (corresponding to a corner cube 3003 in FIG. 30) holds the corner cube offset by 0.005 inch from the centerline of the housing support frame. The type 3 mount (corresponding to a corner cube 3005 in FIG. 30) is offset by 0.010 inches from the centerline and the type 4 mount (not shown in FIG. 30) is offset by 0.015 inches from the centerline.
4. Place the type 1 mount with the corner cube in the far side of housing support frame with the face of the cube looking in towards the optics path.
5. Look down the receiving bore to determine if the light source image is centered in the bore.
6. If it is centered, bond the corner cube mount to the housing support frame but do not glue the corner cube to the mount.
7. If the light source is not in the center of the receiving bore, a mount with an offset should be used to center the light source. Begin with the type 2 mount. Install the mount with a corner cube in the housing support frame. Rotate the mount to determine if the source image is aligned in the receiver bore. If it will not align, proceed to the type 3 mount and so on.
8. Look back into the receiver bore at the image. The corner cube itself has line that might be visible. Rotating the corner cube in the mount can eliminate this line.
9. When the image no longer shows any lines, bond the corner cube into the corner cube mount.
10. The last step in this phase is to mount the receiver diode. Place 0.200 inch thick insulation tubing over the positive and negative signal leads.
11. Install the receiver diode into the back of the optics block keeping the leads in line and the positive lead farthest away from the LED.
12. Insert the diode and bond. At this point all the optics have been aligned and sealed in place.

The above process may be performed partially or fully by a technician or may be performed by computerized apparatus.

Figure 34:
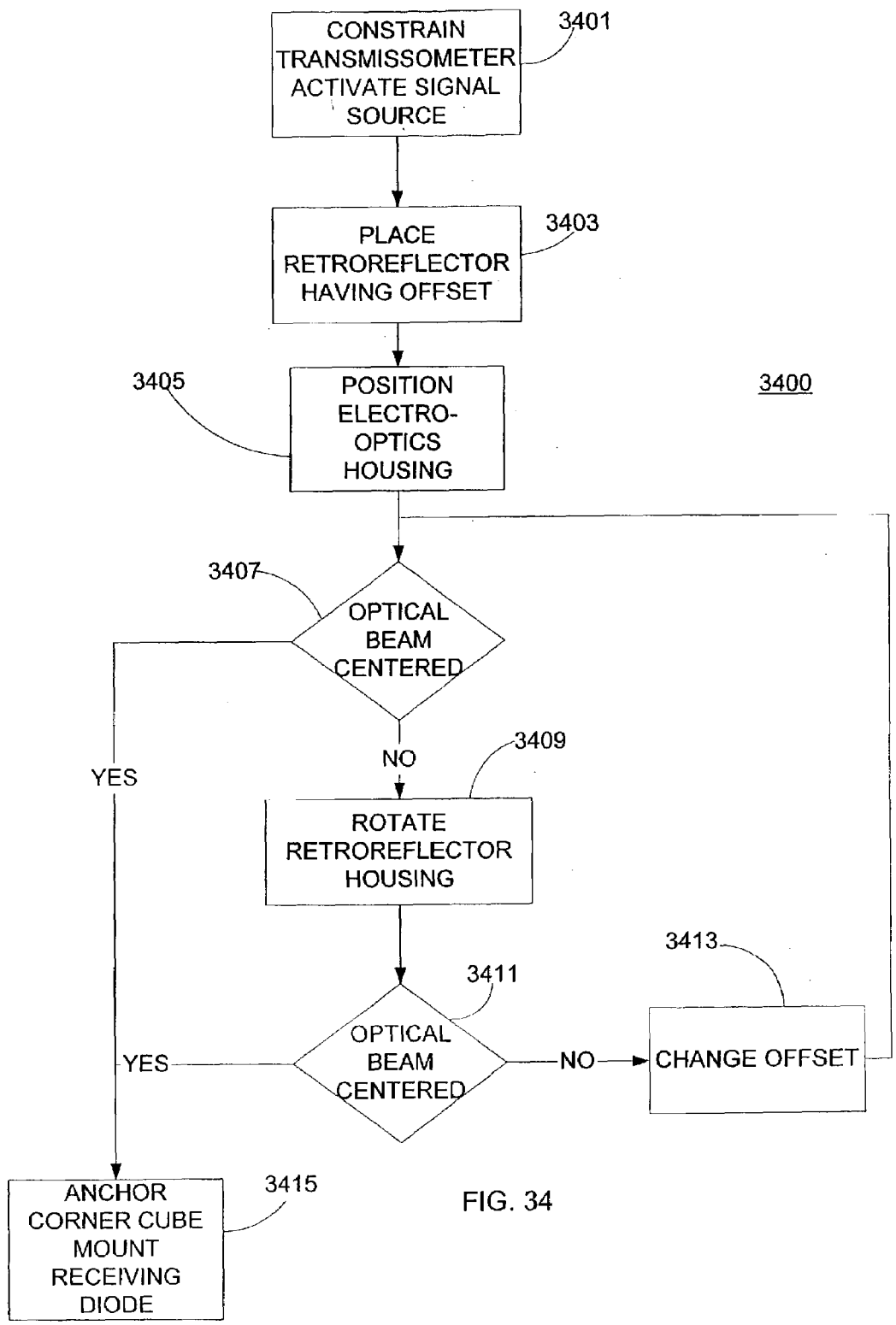
FIG. 34 shows a flow diagram for aligning optics of a beam transmissometer in accordance with an embodiment of the invention.

FIG. 34 shows a flow diagram 3400 for aligning optics of a beam transmissometer in accordance with the above process. In step 3401, transmissometer 400 is constrained the signal source is activated. In step 3403, retroreflector housing 2605 is placed in housing support frame 2607. In step 3405, electro-optics housing 2601. In step 3407, it is verified whether the optics beam is centered. If not, retroreflector housing 2605 is rotated until the optics beam is centered in steps 3409 and 3411. If rotating retroreflector housing 2605 does not center the optics beam, then retroreflector housing 2605 is configured with a different offset. Once the optical beam is centered, step 3415 is performed in which the corner cube is anchored in retroreflector housing 2605 and the receiving diode is mounted. Other components of transmissometer 400 are then assembled.

Data Acquisition

In the embodiment, software measures, displays and records the signal generated by transmissometer 400. The software functions by triggering a counter on the rising edge of each pulse in the frequency signal emanating from the transmissometer. The counter runs on the 20 MHz time base until the next rising edge stores and resets the counter value. In this way, each individual pulse period is measured. This provides accuracy that is many orders of magnitude greater than the noise floor of the sensor output. This enables the system to make a frequency measurement as often as every pulse, or the measurements can be averaged over multiple pulses. The interface and utilization of the software is described in the next section.

Figure 35:
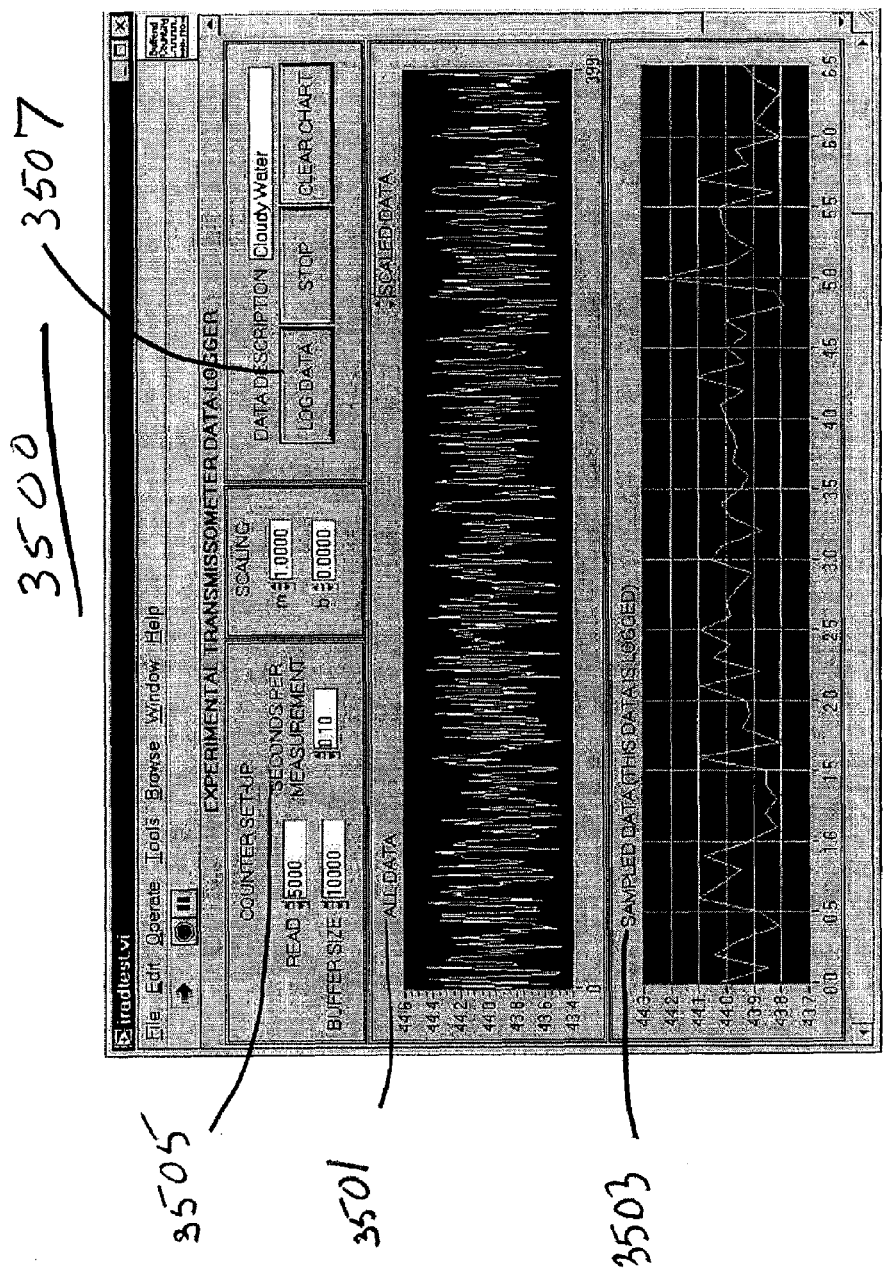
FIG. 35 shows a transmissometer data logger for an expendable probe in accordance with an embodiment of the invention.

FIG. 35 shows a transmissometer data logger 3500 for probe 2100. The data acquisition interface provides two displays for the acquired data. The first display, labeled "ALL DATA" 3501, is used to display every pulse period measurement taken. The data is then averaged and displayed at specific time intervals on the second graph labeled "SAMPLED DATA" 3503. The time interval is set by adjusting the "SECONDS PER MEASUREMENT" 3505 input. The logging feature of the software allows the data to be stored in a file that is easily imported to a spreadsheet. Upon clicking the "LOG DATA" 3507 button, the measurements are continuously written to a file until the "LOG DATA" 3507 button is clicked again to end the data logging. Finally, data may be shown as raw frequency measurements or they may be scaled into engineering units by use of the "m" and "b" scaling factors. Once calibration coefficients have been determined, the coefficients may be entered in the "m" and "b" inputs to scale the incoming frequency data according to the relation:

$$\text{Scaled Data} = m * \text{Frequency} + b$$

This allows real-time display of water transmissivity versus time. In the embodiment, software provides a basis for an end user implementation of an expendable transmissometer data collection system.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

We claim:
1. An apparatus for determining a beam attenuation coefficient of a medium, comprising:
   a signal source that generates a generated optical beam;
   a first arrangement that collimates the generated optical beam to form a projected optical beam;
   a retroreflector that directs the projected optical beam;
   a second arrangement that receives the projected optical beam from the retroreflector and that focuses the projected optical beam to form a focused optical beam;
   a detector that detects a portion of the focused optical beam in order to produce an electrical signal so that the beam attenuation coefficient can be determined;
   a synchronizer that causes the signal source to generate the generated optical beam in a pulsed pattern and that causes the detector to detect the portion of the focused optical beam in concert with the pulsed pattern;
   wherein the signal source comprises a light emitting diode (LED) and wherein the synchronizer comprises:
      a timer that causes the LED to generate the generated optical beam in concert with a pulse rate;
      a lock-in amplifier tat processes the electrical signal in concert with the pulse rate, whereby an effect of distortion that is incurred by the generated optical beam traversing between the LED and the first arrangement, by die projected optical beam traversing between the first arrangement and the second arrangement, and by the focused optical beam traversing between the second arrangement and the detector is ameliorated.

2. The apparatus of claim 1, wherein the lock-in amplifier comprises:
a bandpass filter that amplifies a pulsed component of the electrical signal and attenuates a noise component of the electrical signal;
a mixer that samples the pulsed component of the electrical signal in order obtained a locked signal; and
a low pass filter that converts the locked signal into a baseband signal.

3. The apparatus of claim 2, further comprising:
a transmitter that receives the baseband, determines information about the beam attenuation coefficient, and sends the information to calculating unit.

4. The apparatus of claim 3, wherein the beam transmissometer further comprises the calculating unit.

5. The apparatus of claim 4, wherein the calculating unit comprises a processor and wherein the processor is configured to perform:
(a) determining the beam attenuation coefficient from the information, wherein the beam attenuation coefficient is determined from a pulse period measurement; and
(b) averaging the beam attenuation coefficient is averaged for a plurality of pulse period measurements.

6. The apparatus of claim 5, wherein the processor is configured to perform:
(c) displaying the beam coefficient on a display that is associated with the calculating unit.

7. An apparatus for determining a beam attenuation coefficient of a medium, comprising:
a signal source that generates a generated optical beam;
a first arrangement that collimates the generated optical beam to farm a projected optical beam;
a retroreflector that directs the projected optical beam;
a second arrangement that receives the projected optical beam from the retroreflector and that focuses the projected optical beam to form a focused optical beam;
a detector that detects a portion of the focused optical beam in order to produce an electrical signal so that the beam attenuation coefficient can be determined;
a synchronizer that causes the signal source to generate the generated optical beam in a pulsed pattern and that causes the detector to detect the portion of the focused optical beam in concert with the pulsed pattern;
a processor that receives the electrical signal from the detector, the processor configured to perform:
(a) pulsing the signal source when generating the generated optical beam; and
(b) synchronizing the detector with the generated optical beam;
wherein (b) comprises:
(i) amplifying a pulsed component of the electrical signal in order to reduce a noise component of the electrical signal;
(ii) sampling the pulsed component in order to obtain a locked signal in concert with the generated optical beam; and
(iii) converting the locked signal to a baseband signal.

8. The apparatus of claim 7, wherein the signal source comprises a light emitting diode (LED).

9. The apparatus of claim 8, wherein the generated optical beam has a wavelength between approximately 455 to 575 nanometers.

10. The apparatus of claim 7, wherein the processor configured to perform:
(c) calculating the beam attenuation coefficient from the base and signal.

11. The apparatus of claim 7, wherein the detector comprises:
a photodiode that converts the portion of the focused optical beam.

12. The apparatus of claim 11, further comprising:
a amplifier that compensates for a capacitance associated with the photodiode.

13. The apparatus of claim 7, wherein the medium is selected from the group consisting of a sea water medium, a fresh water medium, and an air medium.

14. The apparatus of claim 7, wherein the apparatus utilizes a diverging collimated beam (DCB) approach.

15. The apparatus of claim 7, wherein the apparatus utilizes a cylindrically limited beam (CLB) approach.

16. The apparatus of claim 7, wherein the retroreflector is situated in a noise/retroreflector housing, and wherein the signal source, the first arrangement, the second arrangement, and the detector are situated in an electro-optics housing, the beam transmissometer further comprising:
a housing support frame.

17. The apparatus of claim 7, further comprising:
a window that seals the first arrangement and the second arrangement from the medium.

18. A beam transmissometer for determining a beam attenuation coefficient of a medium, comprising:
a signal source that generates an optical beam;
a detector that detects a portion of the optical beam to obtain an electrical signal; and
a synchronizer that causes the signal source to generate the optical beam in concert with a pulsed pattern and that causes the detector to detect a portion of the optical beam in concert with the pulsed pattern;
wherein the synchronizer comprises:
a timer that causes the signal source to generate the optical beam in concert with a pulse rate;
a lock-in amplifier that processes the electrical signal in concert with the pulse rate;
wherein the lock-in amplifier comprises:
a bandpass filter that amplifies a pulsed component of the electrical signal and attenuates a noise component of the electrical signal;
a mixer that samples the pulsed component of the electrical signal in order obtained a locked signal; and
a low pass filter that converts the locked signal into a baseband signal.

19. The beam transmissometer of claim 18, wherein the signal source is selected from the group consisting of a light emitting diode (LED) and an optical laser.

20. The beam transmissometer of claim 18, wherein the pulsed pattern is periodic.

21. The beam transmissometer of claim 20, wherein the pulsed pattern has a corresponding frequency between approximately 100 Hz and 500 (n) Hz.

22. The beam transmissometer of claim 18, wherein the pulsed pattern is aperiodic.

23. A beam transmissometer for determining a beam attenuation coefficient in a water medium, comprising:
a light emitting diode (LED) that generates a generated optical beam;

a first arrangement that collimates the generated optical beam to form a projected optical beam;

a retroreflector that directs the projected optical beam;

a second arrangement that receives the projected optical beam from the retroreflector and that focuses the projected optical beam to form a focused optical beam;

a photodiode that detects a portion of the focused optical beam in order to produce an electrical signal;

a synchronizer that causes the LED to generate the generated optical beam in a pulsed pattern and that causes the photodiode to detect the portion of the focused optical beam in concert with the pulsed pattern, wherein the synchronizer comprises:

a timer that causes the LED to generate the generated optical beam in concert with a pulse rate;

a bandpass filter that amplifies a pulsed component of the electrical signal and attenuates a noise component of the electrical signal;

a mixer that samples the pulsed component of the electrical signal in order obtained a locked signal; and a low pass filter that converts the locked signal into a baseband signal; and a transmitter that receives the baseband signal, determines information about the beam attenuation coefficient, and sends the information to a calculating unit.

24. A method for aligning optical components of a beam transmissometer, the method comprising the steps of:

(a) constraining a housing support frame of the beam transmissometer to minimize movement of the housing support frame;

(b) activating a signal source in order to produce an optical beam;

(e) placing a retroreflector mounting into a far side of the housing support frame, wherein a corner cube has a first offset with respect to a centerline of the housing support frame;

(d) positioning an electro-optics housing on a near side of the housing support frame, wherein the electro-optics housing comprises projecting and receiving apparatus for the optical beam;

(e) verifying that the optical beam is centered in a receiving bore of the electro-optics housing;

(f) in response to step (e), if the optical beam is not centered, rotating the retroreflector mounting;

(g) in response to step (f), if the optical beam cannot be centered by rotating the retroreflector mounting, reconfiguring the retroreflector mounting, wherein the corner cube has a second offset; and (h) in response to step (g), repeating steps (e)–(g).

25. The method of claim 24, further comprising the step of:

(i) in response to step (h), anchoring the corner cube in the retroreflector housing.

26. The method of claim 25, further comprising the step of:

(i) in response to step (i), mounting a receiving diode in the receiving bore of the electro-optics housing.

27. The method of claim 24, wherein the first offset and the second offset are selected from the group consisting of approximately zero inches, 0.005 inches, 0.010 inches, and 0.015 inches.

* * * * *

UNITED STATES PATENT AND TRADEMARK OFFICE
CERTIFICATE OF CORRECTION

PATENT NO. : 7,068,362 B2 Page 1 of 1
APPLICATION NO. : 10/348890
DATED : June 27, 2006
INVENTOR(S) : Thomas M. Murdock et al.

It is certified that error appears in the above-identified patent and that said Letters Patent is hereby corrected as shown below:

In the claims,
Column 16, Line 64, replace 'tat' with --that--
Column 17, Line 1, replace 'die' with --the--

Signed and Sealed this

Twenty-eighth Day of November, 2006

JON W. DUDAS
*Director of the United States Patent and Trademark Office*